US006746976B1

(12) United States Patent
Urankar et al.

(10) Patent No.: US 6,746,976 B1
(45) Date of Patent: Jun. 8, 2004

(54) THIN UNTIL WET STRUCTURES FOR ACQUIRING AQUEOUS FLUIDS

(75) Inventors: Edward Joseph Urankar, Maineville, OH (US); Gerald Alfred Young, Cincinnati, OH (US); Mattias Schmidt, Idstein (DE); James Albert Cleary, Indian Springs, OH (US); Matthias Konrad Hippe, Sulzbach/Ts (DE); Giovanni Carlucci, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 186 days.

(21) Appl. No.: 09/665,771

(22) Filed: Sep. 20, 2000

Related U.S. Application Data

(60) Provisional application No. 60/155,962, filed on Sep. 24, 1999, provisional application No. 60/155,966, filed on Sep. 24, 1999, and provisional application No. 60/155,965, filed on Sep. 24, 1999.

(51) Int. Cl.⁷ .................................................. B32B 9/04
(52) U.S. Cl. ....................... 442/155; 442/409; 442/412; 442/413; 442/153; 428/913
(58) Field of Search ................................ 442/153, 155, 442/409, 412, 413; 428/913

(56) References Cited

U.S. PATENT DOCUMENTS

| | | | |
|---|---|---|---|
| 3,512,530 A | 5/1970 | Jones | 128/290 |
| 3,563,243 A | 2/1971 | Lindquist | 128/287 |
| 3,736,931 A | 6/1973 | Glassman | 128/290 R |
| 3,799,758 A | 3/1974 | Franz | 71/86 |
| 3,853,530 A | 12/1974 | Franz | 71/76 |
| 4,140,513 A | 2/1979 | Prill | 71/86 |
| 4,315,765 A | 2/1982 | Large | 71/87 |
| 4,405,531 A | 9/1983 | Franz | 260/501.12 |
| 4,481,026 A | 11/1984 | Prisbylla | 71/86 |

(List continued on next page.)

FOREIGN PATENT DOCUMENTS

| | | |
|---|---|---|
| AU | 595406 | 3/1990 |
| EP | 0 293 208 B1 | 11/1988 |

(List continued on next page.)

OTHER PUBLICATIONS

Wrill et al., "Glyphosphate Toxicity to Common Milkweed and Hemp Dogbane." Weed Science, vol. 25, pp. 275–287, 1977.

Primary Examiner—Elizabeth M. Cole
(74) Attorney, Agent, or Firm—Edward J. Milbrada; Ken K. Patel; Steven W. Miller

(57) ABSTRACT

Disclosed are thin until wet materials that are suitable for use as acquisition members for absorbent articles (e.g., diapers, catamenial products, and adult incontinence devices). Preferred materials according to the present invention are either: 1) fibrous assemblies that utilize wet strength means to stabilize the material or 2) compressed regenerated cellulosic sponges so that, when the material is saturated with an aqueous fluid, it has an expanded wet density of between about 0.04 grams/cm³ and about 0.4 grams/cm³ and an expanded capillary desorption height of less than about 25 cm and a temporary binding means that helps maintain the material at a compressed dry density between about 0.06 grams/cm³ and about 1.2 grams/cm³ until the material is exposed to an aqueous fluid. The ratio of the compressed dry density to the expanded wet density is also greater than about 1.5:1. A suitable process for making the materials and absorbent structures using the materials are also disclosed.

16 Claims, 3 Drawing Sheets

U.S. PATENT DOCUMENTS

| | | | |
|---|---|---|---|
| 4,507,250 A | 3/1985 | Bakel | 260/502.5 |
| 4,554,297 A | 11/1985 | Dabi | 521/178 |
| 4,740,520 A | 4/1988 | Hallenbach et al. | 514/447 |
| 4,822,453 A | 4/1989 | Dean et al. | 162/157.6 |
| 4,861,652 A * | 8/1989 | Lippert et al. | 428/913 |
| 4,888,093 A | 12/1989 | Dean et al. | 162/157.6 |
| 4,898,642 A | 2/1990 | Moore et al. | 162/157.6 |
| 5,118,444 A | 6/1992 | Nguyen | 252/390 |
| 5,137,537 A | 8/1992 | Herron et al. | 8/120 |
| 5,147,345 A | 9/1992 | Young et al. | |
| 5,217,445 A | 6/1993 | Young et al. | 604/381 |
| 5,317,003 A | 5/1994 | Kassebaum et al. | 504/116 |
| 5,389,598 A | 2/1995 | Berk et al. | 504/206 |
| 5,464,807 A | 11/1995 | Claude et al. | 504/206 |
| 5,549,589 A | 8/1996 | Horney et al. | 604/366 |
| 5,563,179 A | 10/1996 | Stone et al. | 521/64 |
| 5,668,085 A | 9/1997 | Forbes et al. | 504/206 |
| 5,683,958 A | 11/1997 | Berger et al. | 504/116 |
| 5,750,468 A | 5/1998 | Wright et al. | 504/206 |
| 5,779,860 A | 7/1998 | Hollenberg et al. | 162/206 |
| 5,800,416 A | 9/1998 | Seger et al. | 604/366 |
| 5,821,195 A | 10/1998 | Sandbrink et al. | 504/206 |
| 5,827,253 A | 10/1998 | Young et al. | 604/369 |
| 5,877,097 A | 3/1999 | West et al. | 442/327 |
| 5,885,572 A | 3/1999 | Gentry et al. | 424/94.5 |
| 5,948,421 A | 9/1999 | Okano et al. | 424/405 |
| 6,015,935 A | 1/2000 | LaVon et al. | 604/378 |
| 6,083,210 A | 7/2000 | Young et al. | 604/367 |
| 6,273,996 B1 | 8/2001 | Hollenberger et al. | |
| 6,296,929 B1 | 10/2001 | Gentile et al. | |

FOREIGN PATENT DOCUMENTS

| | | | |
|---|---|---|---|
| EP | 0 834 297 A1 | | 4/1998 |
| WO | 95/33379 | | 12/1995 |
| WO | 97/05779 | | 2/1997 |
| WO | 97/31890 | | 9/1997 |
| WO | WO 97/34559 | | 9/1997 |
| WO | 97/36494 | | 10/1997 |
| WO | 98/00084 | * | 1/1998 |
| WO | 98/24313 | | 6/1998 |
| WO | 98/53680 | | 12/1998 |
| WO | 99/05914 | | 2/1999 |
| WO | 99/00012 | | 3/1999 |
| WO | 99/21423 | | 5/1999 |
| WO | WO 99/32060 | | 7/1999 |
| WO | 00/15037 | | 3/2000 |
| WO | WO 00/21476 A1 | | 4/2000 |

* cited by examiner

THIN UNTIL WET STRUCTURES FOR ACQUIRING AQUEOUS FLUIDS

This application claims the benefit of U.S. Provisional Patent Application Serial Nos. 60/155,962, 60/155,965 and 60/155,966, filed in the names of Urankar. et al. on Sep. 24, 1999.

TECHNICAL FIELD OF THE INVENTION

This application relates to materials suitable for use in articles directed to absorbing body fluids. The application particularly relates to materials capable of rapidly acquiring aqueous fluids (e.g., urine, menses, etc.) and preferably releasing such fluids to fluid distribution and storage materials.

BACKGROUND OF THE INVENTION

The development of highly absorbent articles for use as disposable diapers, adult incontinence pads and briefs, and catamenial products such as sanitary napkins is the subject of substantial commercial interest. The ability to provide high performance absorbent articles such as diapers has been contingent on the ability to develop relatively absorbent cores or structures that can acquire, distribute and store large quantities of discharged body fluids, in particular urine where a wearer may expel a large quantity of fluid very quickly (typically called a "gush") and, at the sane time, provide desirable fluid handling properties so as to keep the wearer's skin dry and comfortable. These three functions can be accommodated by specific portions of the absorbent articles optimized for each. An acquisition material (or layer) is designed to take in fluid rapidly during a gush. The acquisition material also has sufficient capillary pressure to pull residual fluid away from adjacent layers (e.g., a topsheet). The gush fluid is stabilized prior to being given up to the distribution material. An optional distribution material (or layer) has sufficient capillary pressure (described in more detail below) to pull fluid away from the acquisition member and distribute it toward the front and rear of the absorbent article, often against the force of gravity to a height of 10–20 cm according to the size of the core. The storage member (or layer) has the highest capillary pressure and may comprise hydrogel-forming absorbent polymers or HIPE-derived hydrophilic absorbent foams to pull the fluid away from any distribution layer that may be present and store the fluid "permanently" away from the skin of the wearer.

Significant effort has been devoted towards the development of superior fluid acquisition and storage components. For example, U.S. Pat. No. 4,898,642 (Moore et al.) issued Feb. 6, 1990, U.S. Pat. No. 4,888,093 (Dean et al.) issued Dec. 19, 1989, U.S. Pat. No. 5,137,537 (Herron et al.), U.S. Pat. No. 5,217,445 (Young et al.), issued Jun. 8, 1993, and U.S. Pat. No. 4,822,453 (Dean et al.) describe curly, stiffened fibers that, when formed into low density webs, do not collapse when wet and retain their ability to acquire fluids at high rates as is experienced in a "gush" situation during urine voiding. Certain types of polymeric foams have been used in absorbent articles for the purpose of actually imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,520 (Garvey et al.), issued Apr. 26, 1988 (absorbent composite structure such as diapers, feminine care products and the like that contain sponge absorbents made from certain types of super-wicking, crosslinked polyurethane foams). U.S. Pat. No. 5,563,179 (Stone et al.) issued Oct. 8, 1996, describes hydrophilic absorbent foams useful for acquiring and distributing aqueous fluids in, e.g., absorbent cores. Similarly, various nonwoven materials have been proposed for fluid acquisition. Of key importance is the ability of these materials to acquire fluids repeatedly in use, to survive storage in a compressed state, and to release the acquired fluid to a subsequent fluid distribution or storage material.

The desirability of reducing the bulk of an absorbent article in the crotch area thereof is also well known. For example commonly assigned U.S. Pat. No. 5,549,589, issued to Horney, et al. on Aug. 27, 1996, commonly assigned U.S. Pat. No. 5,800,416, issued to Seger, et al. on Sep. 1, 1998, and copending, commonly assigned U.S. patent application Ser. No. 08/825,072, filed Mar. 27, 1997 by G. Young et al., Ser. No. 08/825,071, filed Mar. 27, 1997 by G. LaVon et al., and Ser. No. 08/826,208, filed Mar. 27, 1997 by G. Young et al. are all directed to materials that distribute acquired body fluids from the crotch area of an absorbent article to other parts of the absorbent article which allows a reduction in crotch size.

The art has also recognized the desirability of keeping the crotch area of an absorbent article as thin as possible.

U.S. Pat. No. 5,779,860, issued to Hollenberg, et al. on Jul. 14, 1998 describes through air dried tissue structures that are said to expand substantially when wetted. The tissue structures comprise chemithermomechanical pulp and a wet strength resin and are calendered to significantly increase density and reduce caliper. While the '860 patent states that the calendered web can increase in caliper 200 to 600% when fully wetted or saturated, such increased caliper is determined by saturating the web with no confining pressure, drying the web, and measuring the caliper of the dried web. While such increases may be substantial, they are not predictive of the performance of a material useful as a component of a core in an absorbent article where any fluid insult will typically happen while the core is under pressure (e.g., due to the wearer sitting or lying down). Such wearer-applied pressure results in a need to expand against such a confining pressure.

U.S. Pat. No. 5,877,097, issued to West, et al. on Mar. 2, 1999 describes densified webs comprising cellulose fibers and a bonding agent that are formed at a low density and compressed to a higher density. The webs are said to have an absorbent capacity that is superior to prior densified and bonded webs. While such webs may have superior absorbent capacity (on a gram of fluid/gram of absorbent basis), there is no indication that the webs can acquire such fluids quickly enough for use as an acquisition member or that such webs would be able to release acquired fluids to other components for ultimate storage.

The art has also considered sponges as an expansive absorbent medium. For example, a sanitary napkin is described in U.S. Pat. No. 3,512,530, issued to Jones on May 19, 1970, where a compressed regenerated cellulose sponge layer is bonded to a larger fibrous cellulose layer to form a multi-ply absorbent core. The compressed regenerated cellulose sponge layer is positioned over the fibrous layer, and it is typically centered about it; it is intended as the primary absorbent element of the sanitary napkin, while the fibrous layer acts as a secondary or back up absorber. The sanitary napkin described therein is said to be thin prior to use, as compared to other sanitary products having the same absorbent capacity. However, because the sponge layer is intended to provide the primary absorbent capacity, fluid would only wick into the backup fibrous layer after the sponge is substantially saturated with resulting risk of rewet because the underlying layer does not absorb fluid from the sponges.

In another use of sponges, EP Patent 293 208 B1, granted to the Lion Corporation on Jul. 24, 1991, describes the use of multiple layers of compressed regenerated cellulose sponge sheets in a sanitary napkin as the sole absorbent material. Because the sponge serves as the sole absorbent material in the sanitary napkin, the focus is on providing multiple layers of sponge material for softness and there is no recognition therein of the importance of the fluid handling properties that are necessary for a material to be suitable for use as an acquisition material in an absorbent article.

There have also been several attempts to create a fluid-activated acquisition zone in absorbent articles by taking advantage of the swelling of hydrogel-forming absorbent polymers in an inhomogeneous structure to create void volume. See for example PCT Application Serial No. WO 97/34559, published in the name of Lash et. al. on Nov. 19, 1997 and U.S. Pat. No. 5,855,572, issued to Schmidt on Jan. 5, 1999. Such structures are, however, not effective during the first loading of the article because the swelling of hydrogel-forming polymers is too slow to rapidly acquire the deposited bodily fluids, such as urine, and, therefore, only provide void space for subsequent gushes. Further, the void volume provided by such structures does not contain fibers to temporarily immobilize the deposited fluid for subsequent absorption by other core components.

Other examples of absorbent structures including expansive components include U.S. Pat. No. 3,736,931, issued to Glassman on Jun. 5, 1973, which discloses a sanitary napkin having an outer layer of a soft nonwoven moisture absorbent material and an inner layer of a highly compressed fluid absorbent material (the compressed material is not described in any greater detail) with a layer of impervious material therebetween. The napkin preferably is V-shaped in cross section. When the napkin is worn, menses is first absorbed by the compressed layer. Swelling of the compressed layer caused by such absorption is said to expand the outer non-compressed layer thereby adjusting the sanitary napkin to each wearer. In this structure, the compressed layer becomes substantially saturated before absorption of fluids by other layers because of the impervious material that is located between the two absorbent layers. That is, fluid is not substantially pulled away from the compressed layer into another for further distribution and there is a substantial risk of rewet as the compressed layer becomes saturated.

Another example of a compressed absorbent material that is said to expand rapidly on insult, can be found in PCT application WO 99/32060 published in the name of Kimberly-Clark Worldwide, Inc., on Jul. 1, 1999. Described therein are fibrous carded or air laid webs which include a binder. The fibers comprise a blend of cellulosic (rayon or cotton) fibers and non-cellulosic (polyolefin, polyester, and polyamide) and the binder is said to be moisture sensitive and can comprise hydrogen bonding, a non-aqueous solution, a powder, or a material in a fibrous form. The '060 application indicates that the web is compressed to a density of up to about 0.3 g/cc and further indicates that, when wetted, the web should expand rapidly to greater than 80% of its uncompressed thickness. While desirable properties and objectives are described in the '060 application, the application gives no indication that such properties can be achieved. For example, it is known that densification can permanently rearrange fibers to a higher density configuration and the application fails to indicate that the densified webs described therein actually expand rapidly to a lower density. Rather it indicates that the webs are formed at a lower density, densified and that the densified webs should expand rapidly.

Thus, there is a need for materials that are thin and of low bulk for use as core components in absorbent articles. There is a further need for such materials to have useful fluid handling properties that are suitable for a particular use. For materials that are intended for use as an acquisition component in the core of an absorbent article there is a need for materials that can acquire aqueous fluids quickly and that readily "give up" such fluids to other core components while the material is under a confining pressure. There is a further need for such materials to be soft and body conforming to provide fit and comfort. There is also a continuing need for improved absorbent articles that make use of such materials.

SUMMARY OF THE INVENTION

The present invention comprises a thin until wet material that is particularly useful for use as an acquisition member of an absorbent article (e.g., diapers, catamenial products, and adult incontinence devices). Suitable materials according to the present invention include fibrous assemblies that utilize wet strength means to stabilize the assembly and compressed sponges. The material is further provided with a temporary binding means to hold it in a thin state until it is exposed to an aqueous fluid. When the material is exposed to an aqueous fluid, the temporary binding means releases and the thin until wet material can expand to the expanded wet density. When the material is saturated with an aqueous fluid it has an expanded wet density of between about 0.04 grams/cm$^3$ and about 0.4 grams/cm$^3$ and an expanded capillary desorption height of less than about 25 cm and a temporary binding means that helps maintain the web at a compressed dry density between about 0.06 grams/cm$^3$ and about 1.2 grams/cm$^3$ until the material is exposed to an aqueous fluid. The ratio of the compressed dry density, to the expanded wet density is also greater than about 1.5:1. Crosslinked cellulose fibers are particularly preferred fibers for use in the fibrous assembly. The fibrous assembly may further comprise high surface area cellulosic fibers and/or resilient synthetic fibers. Particularly preferred wet strength means comprise papermaking wet strength resins. Particularly preferred temporary binding means for the fibrous assembly comprise a water soluble/water dispersible polymer. Preferred sponges comprise compressed regenerated cellulosic sponges.

A preferred process for making the fibrous webs comprises wet laying the fibrous assembly in the presence of a wet strength means; drying the wet laid nascent thin until wet web; providing the nascent thin until wet material with temporary binding means; densifying the nascent thin until wet material to a compressed dry density; and activating the temporary binding means to help maintain the densified structure. Preferably, the densified structure is further processed to increase the softness thereof.

The process for providing sponge-based thin until wet materials comprises producing a regenerated cellulosic sponge using means known to the art. Once the sponge has been formed, it is dried and compressed to a predetermined density using heated compression means.

The present invention further provides absorbent structures suitable for use in absorbent articles, such as diapers, incontinent briefs, training pants, diaper holders and liners, feminine hygiene garments, and the like, designed to provide improved fit and comfort for the wearer while adequately containing body exudates. Such an absorbent article typically comprises a liquid pervious topsheet, a substantially liquid impervious backsheet, and an absorbent core disposed between the topsheet and the backsheet. The absorbent core is designed so as to be relatively narrow and thin in the crotch area, even when the core absorbs significant amounts of fluid during use. To achieve this, the absorbent core is designed such that absorbed fluid is moved substantially from the crotch region to the front and/or rear waist regions of the article and further comprises the thin-until-wet acquisition material of the present invention.

DETAILED DESCRIPTION OF THE INVENTION

Figure 1:
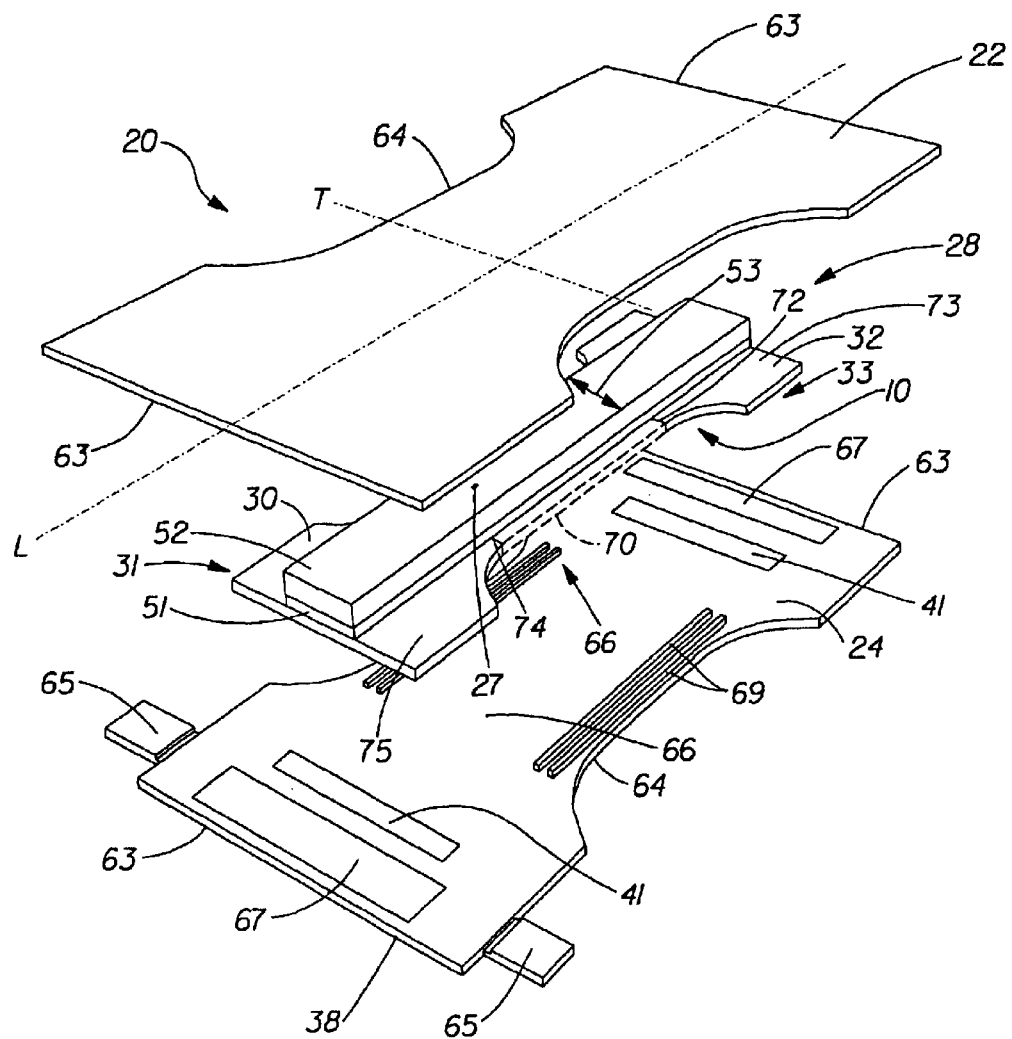
FIG. 1 of the drawings is a blown-apart view of a diaper having an absorbent core which comprises a high capillary suction capacity storage component of the present invention.

I. Characteristics Important to Thin Until Wet Acquisition Structures

A. Density

Density of an acquisition material (i.e., in grams of material per cubic centimeter of material volume) is important because it is a measure of material thickness that normalizes the basis weight of the material.

Any suitable gravimetric procedure that will provide a determination of mass of solid material per unit volume (in either the wet or dry state) of a structure can be used to measure density. The method described in the Test Methods section below is based on an ASTM gravimetric procedure. In its collapsed dry state, the thin until wet structures of the present invention have compressed dry density values in the range of from about 0.06 to about 1.2 g/cm$^3$, preferably from about 0.06 to about 0.8 g/cm$^3$, more preferably 0.06 to about 0.4 g/cm$^3$. In its expanded wet state, the thin until wet structures of the present invention have expanded wet density values in the range of from about 0.04 to about 0.4 g/cm$^3$, preferably from about 0.04 to about 0.3 g/cm$^3$, more preferably 0.04 to about 0.1 g/cm$^3$.

It is also important that the process used to form the thin until wet materials of the present invention (see below for a description of a preferred process) not comprise a step that may limit the expansion capability of the structure. For example, in a process where a material is first created in a low density state and then compressed to a higher density, the compression step should only minimally cause permanent deformation to the initial uncompressed structure. Such permanent deformation can be monitored by the ratio of compressed dry density to expanded wet density. Suitably, the thin until wet structures of the present invention have a ratio of compressed dry density to expanded wet density of greater than about 1.5:1, preferably, the ratio is greater than about 2:1, more preferably the ratio is greater than about 3:1.

B. Capillary Pressure

As used herein the term "capillary pressure" refers to the hydrostatic pressure (also called hydrostatic head, or water column height) at which the fluid loading is measured. In general, a material's ability to absorb fluid and its ability to retain fluid upon desorption may be measured. The term Medium Capillary Pressure refers to the pressure at which the material is at 50% saturation with respect to its 0 cm capacity. Since pressure might be expressed as height of a water column, the present application uses height as a preferred measure of pressure. In the case of the present invention, it is desired to define a medium height to indicate the height at which 50% of the 0 cm absorption absorbent capacity of an absorbent structure under equilibrium conditions at 22° C. is attained. Medium capillary pressures can be expressed either as a medium capillary absorption height (CAH) or as a medium capillary desorption height (CDH) depending on whether the absorbent capacity is determined under absorbing (CAH) or desorbing (CDM) conditions. The underlying theory is described by P. K. Chatterjee and H. V. Nguyen in "Absorbency," Textile Science and Technology, Vol. 7; P. K. Chatterjee Ed.; Elsevier: Amsterdam, 1985. Both CAH and CDH are determined according to the Capillary Sorption method described in the Test Methods section below.

CAH is important because, when the thin until wet materials of the present invention are used as an acquisition component, the materials must be able to acquire fluids from adjacent components of the absorbent article (e.g. the topsheet or a secondary topsheet). In order to be able to acquire, CAH is preferably greater than at least a portion of the desorption pressures of any adjacent structure. It has been found that for the thin until wet materials of the present invention CAH is suitably greater than about 3 centimeters, preferably greater than about 5 centimeters. A method for determining CAH is given in the Test Methods section below.

CDH is important relative to controlling acquired fluid and to the absorption pressure of other absorbent components, especially those intended for fluid distribution or storage. If the fluid acquisition component of an absorbent article holds the acquired fluid too tenaciously, this will inhibit the ability of these other components to partition fluid away. In addition too great a CDH could lead to fluid rewet since too much fluid is held in the acquisition component. This can cause the acquisition component to remain so heavily loaded with fluid that it may not be able to rapidly acquire fluid from subsequent gushes making the absorbent article more susceptible to leaking. Conversely, if the acquisition component cannot control the acquired fluid against gravity, wearer motion could cause fluid flow within the acquisition component that leads to leakage adjacent the edges thereof. Suitably, the thin until wet material of the present invention has a capillary desorption height (CDH value) of not more than about 25 cm, preferably not more than about 20 cm, more preferably not more than about 15 cm, and still more preferably not more than about 12 cm. CDH values should also be greater than about 5 cm to control acquired fluids against the influence of gravity. Typically, the thin until wet material will have a CDH value of from about 5 cm to about 25 cm, more typically from about 5 to about 20 cm, still more typically from about 10 to about 15 cm. A method for determining CDH is given in the Test Methods section below.

C. Compressed Initial Z-Direction Expansion Rate

While a material that may be used as an acquisition member may be desirably thin in the dry state and have a desirable low expanded wet density, the path from compressed dry density to expanded wet density is also important. Specifically, any material that is to be useful as an acquisition component in an absorbent article must be able to acquire body fluids that are deposited onto the absorbent article quickly enough so that the fluids do not run across the body surface of the absorbent article to an edge thereof where such fluids may leak and soil bedding, a wearer's clothing, and the like.

Typically, the art has measured such a property by an acquisition test whereby the rate at which an absorbent structure is able to absorb a fluid deposited thereon is measured. The fluid is usually provided to the absorbent structure at a fairly high rate to simulate the "gush" of fluid from, for example, a urination. Frequently, the absorbent structure is challenged by a series of "gushes" to simulate multiple urination episodes between changes and to measure the performance of a partially loaded absorbent structure. One of skill in the art will recognize that such acquisition rates depend, not only on the structure of any acquisition member of an absorbent structure that is being evaluated, but also on the ability of any underlying structure to rapidly partition fluid away from the acquisition member.

A thin until wet structure according to the present invention must, on exposure to an aqueous fluid, quickly expand from a compressed dry density to an expanded wet density wherein the expanded wet density is low enough to provide for fluid acquisition before the risk of leakage due to surface run off becomes unacceptably high. In other words, the thin until wet structures of the present invention should have a compressed initial z-direction expansion rate of at least about 0.5 millimeters/second, preferably the compressed initial z-direction expansion rate is at least about 0.75 millimeters/second, more preferably, at least about 1 millimeter/second, still more preferably at least about 2 millimeters/second. A method for compressed initial z-direction expansion rate is given in the Test Methods section below.

D. Capacity

It is further desirable for material that is used as an acquisition member to provide sufficient absorbent capacity to be able to acquire a "gush" of body fluid. The average gush size for toddlers in the weight range between 20 and 40 pounds (9 and 18 kilograms) is about 75 milliliters, the 95 percentile of the gush size for this user group is about 110 milliliters. In contrast, the average gush size of an incontinent adult is about 180 milliliters. For the purposes of this invention, the absorbent capacity of the thin until wet materials of the present invention is be quantified by amount of synthetic urine absorbed at zero hydrostatic head in the Capillary Sorption test described in the Test Methods section below. Preferably, the thin until wet material has an absorbent capacity of at least 80 percent of the average gush volume of an intended user group, more preferably the absorbent capacity is at least 100 percent of the average gush volume of the intended user group, most preferably the absorbent capacity is equivalent to at least the 95 percentile of liquid gushes of the intended user group.

As will be recognized, the absolute capacity of an absorbent structure depends on both the dimensions of the structure and on the properties of the material itself. The desirability of thin, narrow core structures places particular demands on an absorbent structure that is intended to be an acquisition member because of the need to minimize dimensions. It has been found that a suitable thin until wet material according to the present invention should have a capacity of at least 9 grams of synthetic urine per gram of thin until wet material when the material is fully saturated at a zero hydrostatic head in the Capillary Sorption Test described below. Preferably, the material should have a capacity of at least about 12 grams/gram, more preferably at least about 14 grams/gram.

E. Capacity per Dry Unit Volume

As will be recognized from the foregoing, a material having a high capacity for body fluids per unit dry volume would be particularly desirable because it would be thin until it becomes wetted with such fluids. As will be further recognized, a thin until wet material, as described herein, will have such capacity because it remains in a compressed (i.e., thin) state until it is wetted by a body fluid at which time it expands to absorb such fluids as may be deposited thereon. A suitable thin until wet material has a capacity per unit dry volume of at least about 1.0 gram per dry $cm^3$ of material. Preferably, a material according to the present invention has a capacity per unit dry volume of at least about 1.5 grams per dry $cm^3$ of material more preferably at least about 2.0 grams per dry $cm^3$ of material. Capacity per unit dry volume of a material is determined according to the method described in the Test Methods section below.

F. Softness

In addition to being thin when dry and having the desirable fluid handling properties that are described above, preferred materials for consumer absorbent products are also soft. Such softness provides increased comfort during wear. As is well known softness is a subjective, multi-faceted property including components such as bending resistance, buckling resistance and coefficient of friction. As is also known the tensile properties of a material are also important as a predictor of softness. In particular, materials having a low tensile modulus and high elongation are desirable.

Bending and buckling resistance are particularly important properties for a core component of an absorbent article because such components typically do not directly contact a wearer's skin (no skin contact means any direct contact-related softness components such as coefficient of friction are of lower importance) and because core components are frequently thicker than other components of an absorbent article (as is known, bending resistance is a third order function of thickness). However, while low bending resistance is desirable, it is not sufficient. For example, when a material with low bending resistance is in an arcuate configuration, resistance to crushing or buckling increases substantially.

An especially desirable measure of the bending component of softness in the case of absorbent article core components has been found to be buckling resistance. As will be recognized by one of skill in the art, the core of an absorbent article assumes an arcuate configuration when it is worn because of the need to conform to a wearer's anatomy. The Bulk Softness test described in the Test Methods section below uses resistance to compressive deformation of a sample having a controlled arcuate configuration as a measure of the softness of the sample. Suitably, a thin until wet structure according to the present invention has a buckling force of less than about 3 Newtons. Preferably, the buckling force is less than about 2 Newtons, more preferably, less than about 1 Newton.

G. Other Performance Parameters of Interest

As will be recognized, skin dryness is an important property for any absorbent article. A particularly useful measure of skin dryness is described in U.S. Pat. No.

6,085,579, issued to Herrlein on Jul. 11, 2000. Suitably, absorbent articles that are evaluated using this method to have a value of less than 150 mg. It is particularly desirable for absorbent articles that are evaluated using this method to have a value of less than 100 mg, more preferably less than about 50 mg.

Desirably, an acquisition structure will be able to spread body fluids that are deposited thereon to regions of the structure that are remote from the immediate point of the insult. Such ability makes more efficient use of the acquisition structure and prevents the region of the structure from being prematurely saturated. In one aspect such spreading ability is related to a low resistance to flow so the minimal hydrostatic head that occurs during the "gush" provides a sufficient driving force for spreading. Flow resistance can be measured according to the method described in PCT application WO 00/00118, published in the name of Procter & Gamble on Jan. 6, 2000. Suitably, an acquisition material will have a permeability as measured according to the method described therein of at least about 10 Darcy. Preferably, the permeability is at least about 50 Darcy, more preferably at least about 100 Darcy.

II. Preferred Thin Until Wet Structures

A. Overview

As noted above, the thin until wet structures of the present invention must have several properties so that they have desirable low bulk when dry and desirable fluid handling properties when wetted with an aqueous fluid. Such requirements help to define the structure of the thin until wet materials of the present invention. As noted above, suitable materials include, but are not limited to fibrous assemblies having both wet strength means and a temporary binding means and compressed regenerated cellulose sponges.

B. Fibrous Assembly

1. General

In general, the structures of the present invention comprise a fibrous assembly that is held together using both wet strength means and temporary binding means. The fibrous assembly provides the main structure for the fluid handling properties (e.g. expanded wet density, expanded desorption pressure) of the thin until wet materials of the present invention. The wet strength means connect the fibers comprising the fibrous assembly to help maintain them in an arrangement that has desirable fluid handling properties after the structure has been exposed to an aqueous fluid. The temporary binding means helps maintain the thin until wet material at a compressed density that is greater than the expanded wet density and, because such means are sensitive to aqueous fluids, releases the structure for expansion on exposure thereto.

The thin until wet materials of the present invention suitably comprise from about 75% to about 99% fibers in a fibrous assembly, from about 0% to about 10% of a material suitable for use as a wet strength means, and from 0% to about 20% of a material suitable for use as a temporary binder. All percentages herein refer to weight percentages based on total dry material weight. Preferably, the thin until wet materials will comprise between 85% to about 99% fibers in a fibrous assembly, from about 0.1% to about 5% of a material suitable for use as a wet strength means, and from 0% to about 10% of a material suitable for use as a temporary binder. More preferably, the thin until wet materials will comprise 90% to about 99% fibers in a fibrous assembly, from about 0.1% to about 2% of a material suitable for use as a wet strength means, and from 0% to about 5% of a material suitable for use as a temporary binder. The three basic components of these thin until wet materials are described in greater detail below.

2. Fibers

As noted above, the thin until wet materials of the present invention comprise a fibrous assembly so as to provide basic fluid handling properties to the material. As will be recognized, the fibers comprising the fibrous assembly should be substantially hydrophilic so that they are readily wetted by aqueous fluids. Suitable fibers include several different materials including synthetic fibers such as polyester, polypropylene, or polyethylene (one of skill in the art will recognize that it may be necessary to treat such synthetic fibers to increase the hydrophilicity thereof—e.g., with a surfactant); semi-synthetic fibers, such as rayon; natural fibers including wood fibers, cotton, or cellulose; blends of such fibers; or any equivalent materials or combinations of materials.

Particularly preferred are curly, stiffened fibers formed from crosslinked cellulose that, when converted into low density structures, do not collapse when wet and retain their ability to acquire fluids at high rates as is experienced in a "gush" situation during urine voiding. Such fibers are described in, for example in U.S. Pat. No. 4,898,642 (Moore et al.) issued Feb. 6, 1990, U.S. Pat. No. 4,888,093 (Dean et al.) issued Dec. 19, 1989, U.S. Pat. No. 5,137,537 (Herron et al.), U.S. Pat. No. 5,217,445 (Young et al.), issued Jun. 8, 1993, and U.S. Pat. No. 4,822,453 (Dean et al.). Especially preferred are the individualized, crosslinked cellulosic fibers having an effective amount of a polyacrylic acid crosslinking agent as described in commonly assigned, copending U.S. patent application Ser. No. 08/692,352, filed in the name of Heron, et al. on Aug. 5, 1996, the disclosure of which is incorporated herein by reference.

Since the fibrous assembly provides the basic fluid handling properties of the thin until wet materials of the present invention, the material should comprise the maximum quantity of fibers that is consistent with the other performance criteria described above. Suitably, the thin until wet materials of the present invention will comprise between about 75% and about 99% fibers, preferably between about 85% and about 99% fibers, more preferably between about 90% and about 99% fibers.

In some instances it may also be desirable for the fibrous assembly to comprise a proportion of high surface area fibers. Such fibers are particularly desirable when the fibrous assembly predominately comprises curly, stiffened fibers so as to provide bonding sites for the wet strength means and the temporary bonding means. Suitable high surface area fibers include microfibrous cellulose, nonstiffened cellulosic fibers (i.e., conventional cellulosic pulp fibers, particularly eucalyptus fibers), highly refined, stiffened and nonstiffened, cellulosic fibers (preferably with Canadian Standard Freeness (CSF) of less than about 200 CSF, more preferably from about 40 CSF to about 100 CSF) referred to herein as "crill". Additional high surface area fibers are described in the aforementioned U.S. Pat. No. 5,217,445. Such high surface area fibers should be used at the minimum level necessary for satisfactory mechanical property development because they cause an undesirable increase in CDH. Suitably, between about 0% and about 15% of the fibers comprising the fibrous assembly comprise high surface area fibers, preferably between about 0% and about 10%.

It may also be desirable for a portion of the fibers in the fibrous assembly to comprise non-cellulosic fibers. For example, synthetic fibers comprising polymeric materials such as polyamide, polyester, polypropylene, polyethylene, or polyurethane may be used in relatively small amounts to provide additional resiliency to the structure. Particularly preferred for this use are polyester staple fibers. Only as much synthetic fiber as is necessary to provide the desired resiliency should be used in order to maximize the fluid handling properties of the thin until wet materials of the present invention. Suitably, such materials may comprise from about 0% to about 30% of a suitable synthetic fiber. Preferably, the materials of the present invention comprise from about 0% to about 20% of a suitable synthetic fiber. One preferred synthetic fibrous material is a polyester fiber such as DACRON® or KODEL®. A particularly preferred synthetic fiber is the polyester staple available from KoSa Nonwovens, inc. of Salisbury, N.C. as T-224.

3. Wet Strength Means

As noted above, the wet strength means connects at least a portion of the fibers forming the fibrous assembly of the thin until wet materials of the present invention to help the fibrous assembly maintain an advantageous fluid handling structure after it has been exposed to an aqueous fluid. In particular, the wet strength means helps maintain the fibers in a relatively constant relationship with each other so that the capillary structure that is formed by interactions between the fibers is maintained after compression and reexpansion.

Without being bound by theory, the following is believed to explain the operation of the wet strength means in helping maintain an advantageous fluid handling structure. As is known (e.g., P. K. Chatterjee and H. V. Nguyen in "Absorbency," Textile Science and Technology, Vol. 7; P. K. Chatterjee, Ed.; Elsevier: Amsterdam, 1985; Chapter 2), the rate of travel of fluid water through a fibrous material is governed by fiber arrangement which controls capillary size and continuity. It is believed that the wet strength means concentrates around at least a portion of the fibrous intersections when the thin until wet structures of the present invention are in a low density state, joining individual fibers at such intersections. The wet strength means serves two functions at such points of joinder when a nascent thin until wet material (As used herein a "nascent" thin until wet material is a one that has been formed into a fibrous assembly but not yet densified to its final dry compressed density.) is compressed from a low density state to a higher compressed dry density as part of a manufacturing process: 1) preservation of capillary structure by prevention of fibers sliding relative to each other to relieve the compressive stress caused by the densification and 2) storage of part of the densification energy by self-deformation at the points of joinder (As will be recognized, additional compressive energy is stored due to bending of individual fibers). When the compressed, thin until wet structure is exposed to an aqueous fluid (As will be discussed below with respect to the temporary binding means, the thin until wet materials of the present invention are held in a compressed state until exposure to an aqueous fluid.), the stored compressive energy is released and the thin until wet material returns to an expanded wet density that is substantially lower than the compressed dry density.

Only as much of a material suitable for use as a wet strength means as is necessary to satisfy the above-identified performance requirements should be used in order to maximize the fluid handling properties of the thin until wet materials of the present invention. Suitably, such structures may comprise from about 0% to about 10% of a material suitable for use as a wet strength means. Preferably, the materials of the present invention comprise from about 0.1% to about 5% of a material suitable for use as a wet strength means. More preferably, the materials of the present invention comprise from about 0.1% to about 2% wet strength means.

Given these performance requirements, suitable materials for the wet strength means preferably: 1) is water resistant (i.e., a suitable material preferably does not suffer a substantial degradation in properties on exposure to an aqueous fluid for the duration of a normal wear cycle for an absorbent article according to the present invention); 2) has sufficient mechanical strength so that interfiber bonds resist breaking when a nascent thin until wet material is first compressed; and 3) is capable of storing a least a portion of the compressive energy by self-deformation. Preferably, a suitable wet strength means is also creep resistant so stored compressive energy is not relieved by molecular rearrangement while the thin until wet material of the present invention is stored at a compressed dry density.

One class of materials that is suitable for use as wet strength means includes materials that are used as wet strength resins in the papermaking industry. Such resins typically form covalent bonds with cellulose via the hydroxyl groups thereon. Exemplary materials include: cationic modified starches having nitrogen-containing groups (e.g., amino groups) such as those available from National Starch and Chemical Corp., Bridgewater, N.J.; latexes, thermosetting polymers; wet strength resins such as polyamide-epichlorohydrin resin (e.g., Kymene® 557H, Hercules, Inc. Wilmington, Del.), polyamide-epichlorohydrin resin (e.g., Amres® 8855, Georgia-Pacific of Atlanta, Ga.), polyallylamine-based epoxides (Kymene® 450, Hercules, Inc. Wilmington, Del.), polyisocyanate-based resins (Isovin, Bayer Corp., Pittsburgh, Pa.), polyacrylamide resins described, for example, in U.S. Pat. No. 3,556,932 (Coscia et al), issued Jan. 19, 1971; commercially available polyacrylamides marketed by Cytec Industries, West Patterson, N.J., under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

Alternatively, the wet strength means can comprise bonding the fibers comprising the fibrous assembly using thermal means. For example a portion of the fibrous assembly can comprise bicomponent fibers wherein the individual fibers comprise two or more thermoplastic polymers, wherein one of the polymers has a lower melting point than the other polymer. After forming, the material can be heated (prior to any compression process step—see discussion below) to a temperature above the melting point of the lower melting thermoplastic polymer using a method as may be known to the art, such as through air bonding or a heated nip and then cooled. Alternatively, a powdered adhesive material may be dispersed throughout the structure and then melted and cooled as described above. It is important that the thermoplastic polymer be heated only to a temperature which fuses the thermoplastic polymer to other fibrous materials, but not so high as to cause the thermoplastic polymer to flow into the void volume of the network. A suitable bicomponent fiber is a crimped fiber from KoSa Nonwovens, Inc. of Salisbury, N.C. commercially available under the tradename CELBOND®. A suitable powdered adhesive comprises particles of high-density polyethylene with maximum dimensions of about 400 microns, characterized by a melt flow index of about 50 g/10 min. as measured according to ASTM method D 1238-85 under conditions 190/2.16. Such powdered adhesives are described in greater detail in commonly assigned U.S. Pat. No. 5,428,761, issued to Palumbo, et al. on Jan. 9, 1996.

4. Temporary Binding Means

The temporary binding means helps maintain the thin until wet material's of the present invention at a desirable compressed dry density until such materials are exposed to an aqueous fluid. Since the nascent thin until wet materials of the present invention have a density that is substantially lower than the compressed dry density, the temporary binding means is provided to such nascent structures and activated during or after a densification step that transforms the structure from a nascent thin until wet material with a relatively low density to a compressed structure having a compressed dry density. The activation step causes the temporary binding means to become effective in helping to maintain the density at the desired compressed dry density.

The thin until wet materials of the present invention should comprise only as much of a material suitable for use as a temporary binding means as is necessary to maintain such structures at a desired compressed dry density. Suitably, such structures may comprise from about 0% to about 20% of a material suitable for use as a temporary binding means. Preferably, the materials of the present invention comprise from about 0% to about 10% of a material suitable for use as a temporary binding means. It will be recognized that, if the temporary binding means comprises an increased level of hydrogen bonding (discussed below) there is no residual added material and the thin until wet material of the present invention would comprise 0% added material to provide a temporary binding means.

In general, a material that is suitable for use as a temporary binding means: 1) has sufficient strength to provide substantial resistance to the stored compressive energy provided by compressing the nascent thin until wet material; 2) is reversible by water or body fluids such as blood, urine, and the like; and 3) is activatible so that it can be applied to the nascent thin until wet material prior to the densification step and treated in some manner so such means helps preserve the density increase provided by the densification step.

In the simplest sense, the temporary binding means can comprise hydrogen bonds that are formed between fibers when the fibers are dried while under compression (It will be recognized that such hydrogen bonding may contribute to resisting the stored compressive energy but that such hydrogen bonds may be insufficient and that additional temporary binding means may be necessary to substantially fully maintain the thin until wet material of the present invention at a suitable compressed dry density). One such temporary binding means that uses hydrogen bonding is to apply a polar liquid, such as water, to the nascent thin until wet web before compressing it. Without being bound by theory, it is believed that such liquids flow to fiber intersections and, if the production process includes a step which evaporates the liquid prior to or during densification, capillary forces caused by the evaporating liquid will draw the fibers at the intersection together increasing the density of potential hydrogen bond sites to a number greater than if the nascent web were only compressed with heating or other means that may cause hydrogen bonds to form between juxtaposed fibers. It has been found that adding water at a level of between about 2% and about 100% of the dry fiber weight provides a beneficial increase in hydrogen bonding. It will also be recognized that, if the polar liquid is a solvent or carrier fluid for other temporary binding means similar benefits can be achieved.

Chemically, suitable materials for use as a temporary binding means comprise various water soluble or dispersible polymers such as polyacrylic acid and salts and copolymers thereof; polymethacrylic acid and salts and copolymers thereof; polyvinyl alcohol; polyethyleneimine; starch; modified starch; modified cellulose; gum acacia/gum arabic; soluble gelatin; etc. Particularly preferred are the sodium salt of polyacrylic acid (A suitable material is available from Polysciences, Inc. of Warrington, Pa. as catalog no. 6568 (nominal $M_w$=2,100)); polyvinyl alcohol (A suitable material is available from Aldrich Chemical, Co. of Milwaukee, Wis. as catalog no. 36,062-7); methylcellulose (METHOCEL A15-LV as is available from Dow Chemical of Midland, Mich.) and hydroxypropylcellulose (METHOCEL 5E).

5. Formation Process

The constituent components of the thin until wet materials of the present invention may be blended together and formed into suitable structures by a variety of methods, including wet-laying methods, air-laying methods, carding, and other methods, of which wet-laying methods are presently preferred.

In general, wetlaid structures can be made by depositing an aqueous slurry of fibers on to a foraminous forming wire, dewatering the wetlaid slurry to form a wet fibrous assembly, and drying the wet fibrous assembly. Preferably, the aqueous slurries of fibers for wetlaying will have a fiber consistency of between about 0.02% and about 2.0%, preferably between about 0.02% and about 0.2%, total slurry weight basis. Deposition of the slurry is typically accomplished using an apparatus known in the art as a headbox. The headbox has an opening, known as a slice, for delivering the aqueous slurry of fibers onto the foraminous forming wire. The forming wire can be of construction and mesh size used for dry lap or other paper making processing. Conventional designs of headboxes known in the art for drylap and tissue sheet formation may be used. Suitable commercially available headboxes include, for example, open, fixed roof, twin wire, inclined wire, and drum former headboxes. Due to the behavior of chemically stiffened, twisted, and curled fibers, particularly their tendency to flocculate in aqueous slurries, certain processing modifications may be required. Such modifications are described in the aforementioned U.S. Pat. No. 5,549,589 and in the aforementioned U.S. Pat. No. 5,800,416.

Once formed, the wet structure is dewatered and dried. Dewatering can be performed with foils, suction boxes, or other vacuum devices or gravitational flow. Typically, dewatering increases the fiber consistency to between about 8% and about 30%, total wet material weight basis, preferably between about 8% and about 23%. Dewatering to consistencies above about 23% may require wet-pressing and is less preferred. After dewatering, the fibrous assembly can be, but is not necessarily, transferred from the forming wire to a drying fabric which transports the structure to drying apparatuses. Drying of the wet fibrous assembly may be accomplished utilizing many techniques known in the art. When thermoplastic binding materials are included in the fibrous assembly, is particularly important that the fibrous assembly be dried thoroughly and uniformly at a temperature which fuses the thermoplastic binding material to other fibrous materials, but not so high as to cause the thermoplastic binding material to flow into the void volume of the network. Drying can be accomplished via, for example, a thermal blow-through dryer, a thermal air-impingement dryer, and heated drum dryers, including Yankee dryers. The wetlaid structures are preferably dried to completion (generally to fiber consistencies between about 95% to about 99%).

The temporary binding means can be applied to the nascent thin until wet material either during the formation of the low density structure or applied directly to the permanently bonded structure by way of spray application. With either method, the temporary binding means contained within the structure is activated during the compression step to help maintain the structure at the compressed dry density provided by such compression.

Densification of the composite structure may be accomplished via a shimmed laboratory platen press, a nip roll unit, a calendar stack, or other densification means as may be known to the art. It is important not to overcompress the nascent thin until wet material because such overcompression can permanently deform the low density structure reducing the potential to recover the full low density of the nascent thin until wet material. Suitably, the nascent thin until wet material is compressed to a density no more than twice the compressed dry density (100% overcompression). Preferably, the compression step provides less than about 50% overcompression, more preferably overcompression is less than about 25%. Ideally, the nascent thin until wet material is not overcompressed. It will be recognized that overcompression may be necessary because the material may "rebound" after the densification pressure is relieved.

Compression of the structure may be carried out at temperatures ranging from ambient temperature to 170° C. to facilitate densification of the low density structures and activation of the temporary binding means.

The flexibility of the fully dried, densified material is preferably increased. Suitable methods of increasing flexibility would include one of several mechanical techniques such as ring rolling, creping, or microcreping using doctor blades (e.g., Micrexing®) or opposed rolls, s-wrapping, rolling with corrugated rolls, or other techniques well known in the art. The process of increasing the flexibility or softness of the structure may be accomplished as part of the material formation process or as a separate post-formation operation. Alternatively flexibility and/or softness may be achieved by using formation methods that provide the structure with regions of differential density or basis weight such as described in U.S. Pat. Nos. 5,245,025 and 5,527,428, issued to Trokhan, et al. on Sep. 14, 1993 and Jun. 18, 1996 respectively and in U.S. Pat. No. 5,277,761 which issued to Phan, et al. on Jan. 11, 1994. Yet another means said to provide softness is to provide a material known to soften (plasticize) individual fibers. Such a means (e.g., glycerine to soften cellulosic fibers) is described in U.S. Pat. No. 5,641,561, issued to Hansen, et al. on Jun. 24, 1997.

In addition to preferred wetlaying processes as described above, it may be desirable under some circumstances to form nascent thin until wet materials according to the present invention by airlaying, carding, or other suitable methods of forming fibrous assemblies as may be known.

B. Sponges

1. Overview

In an alternative embodiment of the present invention the thin until wet material comprises a compressed regenerated cellulose sponge. Examples of cellulosic sponges are described in the aforementioned European Patent EP-B-0 293 208. The regenerated cellulose sponge is a porous material containing a cellulose skeleton. Examples of such sponges include, in addition to sponges consisting of cellulose itself, sponges consisting of a cellulose derivative as viscose, a cellulose ether and a cellulose ester, and sponges consisting of mixtures of those materials. While compressed regenerated cellulosic sponges are well known to the art, to be suitable for purposes of the present invention a compressed regenerated cellulosic sponge must have physical and fluid handling properties as described herein in order that the sponge be thin until wet, able to acquire bodily fluids from overlying structure, such as a topsheet, and able to and able to give up such fluids to structures having a higher capillary pressure so as to become able to accept the next fluid insult. Such sponges may also be treated with a water soluble material as described in U.S. Pat. No. 3,954,493, issued to Battista, et al. on May 4, 1976.

2. Sponge Material

Suitable sponges are available from Spontex, Inc. of Columbia, Tenn. Particularly preferred are material numbers 12330 and 12334 because they lack the very large pores seen in other commercially available sponges (both material numbers have the same pore size distribution and differ only in expanded thickness). As is known in the art, such large pores have very little contribution to acquisition capability because of their low capillary pressure. Thus, the preferred sponge materials have improved acquisition properties (CAH) without significant degradation of desorption properties (CDH).

As noted above, it is preferable that sponge materials used as thin until wet materials according to the present invention have a maximum pore diameter. Such pore size distribution can be controlled by control of the particle size distribution of the salt crystals used as a porogenic material in the formation of the sponge.

The basis weight of the sponge material may be varied as desired to accommodate the needs of the design of a particular absorbent article. Suitably the basis weight of a sponge material for the present invention is between about 300 and 1000 grams per square meter. Preferably, the basis weight is between about 300 and about 800 grams per square meter; more preferably, between about 300 and about 600 grams per square meter. As will be recognized, the thin until wet material can be provided to an absorbent article in more than one layer, each layer having a basis weight less than that listed above, to provide increased flexibility. Such multi-layer, thin until wet materials are within the scope of the present invention as long as the cumulative basis weight is within the defined ranges.

3. Sponge Material Process

The process for providing sponge-based thin until wet materials comprises producing a regenerated cellulosic sponge using means known to the art. By way of example only, a regenerated cellulose sponge may be prepared from a mixture of a viscose solution with reinforcing fibres and a porogenic compound, e.g., crystals of sodium sulfate decahydrate or of another alkali metal salt with a high content of crystallized water, the final pore dimension being related to the particle size distribution of the salt crystals. The viscose solution may be extruded through an extrusion die of the desired section, then let coagulate. It is particularly preferred to use porogenic compounds having a narrow particle size distribution. The material is washed with water after regeneration in order to eliminate the salt and other possible soluble compounds. Once the sponge has been washed, it is dried and compressed to a predetermined density using heated compression means. The compressed regenerated cellulose sponge has a network structure that contains pores created by the solubilization of the porogenic compound during the washing step.

The sponge material is densified to provide the desirable compressed dry density discussed above. Such densification may be accomplished by treating the web using a suitable compression means. One such suitable means is compression of the dry sponge to a desired density using a shimmed platen press, such as is available from Fred S. Carver, Inc. of Menomonee Falls, Wis., that is heated to a temperature 120° C. Alternatively, heated rollers with sufficient residence time in the nip between the rollers is also suitable. Without being bound by theory, it is believed that the combination of heating and pressure with residual water of hydration in the sponge material facilitates formation of hydrogen bonds within the sponge that maintain the sponge material in a compressed state until wetting by an aqueous liquid breaks the hydrogen bonds allowing the sponge to expand.

Alternatively, the sponge may be treated with one of the water soluble or dispersible polymers described with respect to a fibrous assembly above using the methods described in the aforementioned U.S. Pat. No. 3,954,493 to provide a temporary binding means.

In some cases, it may be desirable to modify the properties (particularly the dry density) of commercially available sponge materials to provide a better balance of capacity, acquisition, and desorption. One suitable method to modify the dry density includes the following steps: 1) fully expand the commercially available sponge by saturating it with deionized water; 2) wash the expanded sponge with deionized water to remove residual soluble materials; 3) dry the washed sponge; followed by 4) compression of the dried sponge material as described above.

The flexibility of the fully dried, densified material is preferably increased using methods similar to those described with respect to fibrous assemblies as are described above. Suitable methods include such as ring rolling, creping, or microcreping using doctor blades (e.g., Micrexing®) or opposed rolls, s-wrapping, rolling with corrugated rolls, or other techniques well known in the art.

III. Uses of Thin Until Wet Materials of the Present Invention

A. In General

Thin until wet materials according to the present invention are broadly useful in absorbent cores of disposable diapers. These materials can also be employed in other absorbent articles (catamenial products, adult incontinence products, and the like), especially when there is a need for a thin/discrete absorbent article along with a need to rapidly acquire fluids deposited onto the absorbent article.

B. Absorbent Articles

1. Overview

The thin until wet structures of the present invention are particularly useful in absorbent structures (e.g., absorbent cores or core components) for various absorbent articles. By "absorbent article" herein is meant a consumer product that is capable of absorbing significant quantities of urine, menses, or other fluids, such as aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The thin until wet structures described herein are particularly suitable for use in articles such as diapers, incontinence pads or garments, clothing shields, and the like.

In its simplest form, where the thin until wet structure exhibits sufficient fluid handling capacity, an absorbent article of the present invention need only include a backing sheet, typically relatively liquid-impervious and the thin until wet structure. The components will be associated such that the thin until wet material is closest to the fluid discharge region or insult zone of the wearer of the absorbent article. In other embodiments the absorbent article can also comprise a fluid distribution/storage member or individual members directed to each function that are backed by the backing sheet. Liquid impervious backing sheets can comprise any material, for example polyethylene or polypropylene, having a thickness of about 1.5 mils (0.038 mm), which will help retain fluid within the absorbent article.

More conventionally, these absorbent articles will also include a liquid-pervious topsheet component that covers the side of the absorbent article that touches the skin of the wearer. In this configuration, the article includes an absorbent core made up of an acquisition member comprising the thin until wet structure of the present invention and one or more fluid distribution/storage materials of the present invention positioned between the backing sheet and the topsheet. In a particularly preferred embodiment, the article's absorbent core will comprise a separate fluid storage layer. Each of the topsheet and the various core components are in liquid communication with each other. (As used herein, a component is in liquid communication if a body fluid that is disposed on one of the components of an absorbent article can transfer from that component to another component of the absorbent article—either directly or indirectly through an intervening component. Such transfer can be by capillary flow, gravimetric flow, osmotic pressure or other means as may be known.) Liquid-pervious topsheets can comprise any material such as polyester, polyolefin, rayon and the like that is substantially porous and permits body fluid to readily pass there through and into the underlying absorbent core. The topsheet material will preferably have no propensity for holding aqueous fluids in the area of contact between the topsheet and the wearer's skin.

As indicated, in addition to the thin until wet structures of the present invention, the absorbent core of the absorbent articles herein can also comprise other, e.g., conventional, components or materials. In one embodiment involving a combination of the thin until wet structures described herein and other absorbent materials, the absorbent articles can employ a multi-layer absorbent core configuration where a core layer containing an acquisition member comprising the thin until wet structure of the present invention can be used in combination with one or more additional separate core layers comprising other absorbent structures or materials. These other absorbent structures or materials, for example, can include airlaid or wet-laid assemblies of wood pulp or other cellulosic fibers. These other absorbent structures can also comprise foams, e.g., absorbent foams or even sponges useful as liquid acquisition/distribution components such as those disclosed in aforementioned U.S. Pat. No. 5,563,179.

A preferred embodiment entails a further separation of the various absorbent core components. This preferred absorbent core comprises an acquisition layer comprising the thin until wet structures of the present invention only around the crotch region of the wearer to manage the initial rapid fluid gush. A distribution layer is positioned vertically to the front and back of the acquisition layer so as to wick the fluid out of the crotch region, not just from the front to the back. A distinct storage layer is positioned in a position above the acquisition layer (with an assumed standing position of the wearer where the absorbent article has an arcuate configuration) and is in contact only with the distribution material. The storage absorbent member(s) then must be able to absorb the fluid from the distribution layer, overcoming both the force due to gravity and that due to the desorption pressures of the distribution material. The product so depicted removes fluid from the crotch region within the time provided between insults, leaving the acquisition region relatively dry and ready for further uptake of fluid. This further maintains the shape of the garment and keeps the crotch area relatively dry for better skin health.

Alternative embodiments of absorbent cores according to the present invention can comprise layered structures wherein, in cross section, an acquisition layer comprising a thin until wet structure according to the present invention overlies a storage layer with or without a distribution layer therebetween. Such structures have many of the benefits described in relation to the preferred structure discussed above and are contemplated as being part of the present invention.

FIG. 1 shows a preferred embodiment of a diaper 20 having a longitudinal centerline L and a transverse centerline T in which the topsheet 22 and the backsheet 24 are co-extensive and have length and width dimensions generally larger than those of the absorbent core 28. The topsheet 22 is joined with and superimposed on the backsheet 24 thereby forming the periphery 38 of the diaper 20. The periphery 38 is the outer perimeter or the edges of the diaper 20 and is defined by waist edges 63 and side edges 64.

Diaper 20 further has a crotch area 66 defined by determining the crotch point of core 28 in accordance with the description herein. These regions are defined by determining the crotch point of core 28 in accordance with the description in the TEST METHODS section below. Because of the anatomy of a human wearer, the space between the wearer's legs generally confines the space available for the article in this region. For good fit, an absorbent article should be designed such that it fits well in the crotch area 66. If the width of the article is excessive relative to the crotch width of the wearer, the article may be deformed, which might result in deteriorated performance, and reduced wearer comfort. As discussed below, the crotch point is determined by reference to the wearer's anatomy. For purposes of illustration only, the crotch point of core 28 is depicted as item 27 in FIG. 1. Crotch point 27 is depicted as being located on the longitudinal centerline L of diaper 20 and absorbent core 28. This will generally be the case, regardless of the configuration of the diaper and absorbent core. However, as indicated, crotch point 27 is not located on transverse centerline T in this particular embodiment, though it may be in other diaper/core designs. As is discussed above, once the crotch point 27 of absorbent core 28 is determined, the crotch area 66 is determined by measuring forward from the crotch point 27 a distance of 25% of the core's total length (depicted as transverse line 72) and backward from the crotch point 27 a distance of 25% of the core's total length (depicted as transverse line 74). In this illustration, the crotch area 66 is the region of the core located between transverse lines 72 and 74. As depicted in FIG. 1, absorbent core 28 is shown to have a front region 33, a back region 31, and a crotch area 66. Again, the crotch area 66 of core 28 is dictated by the location of the crotch point 27 in the core. The core 28 further comprises a front waist region 73 which lies longitudinally outboard of transverse line 72 and a rear waist region 75 which lies longitudinally outboard of transverse line 74.

2. Topsheet

The topsheet 22 is preferably positioned adjacent the body surface of the absorbent core 28 and may be joined thereto and/or to the backsheet 24 by any attachment means known in the art. Suitable attachment means are described below with respect to means for joining the backsheet 24 to other elements of the diaper 20. In one preferred embodiment of the present invention, the topsheet 22 and the backsheet 24 are joined directly to each other in some locations and are indirectly joined together in other locations by directly joining them to other elements of the diaper 20.

The topsheet 22 is preferably compliant, soft feeling, and non-irritating to the wearer's skin. Further, at least a portion of the topsheet 22 is liquid pervious, permitting liquids to readily penetrate through its thickness. A suitable topsheet 22 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 22 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, which issued to Thompson on Dec. 30, 1975; U.S. Pat. No. 4,324,246, which issued to Mullane, et al. on Apr. 13, 1982; U.S. Pat. No. 4,342,314 which issued to Radel, et al. on Aug. 3, 1982; U.S. Pat. No. 4,463,045, which issued to Ahr, et al. on Jul. 31, 1984; and U.S. Pat. No. 5,006,394, issued to Baird on Apr. 9, 1991. Other suitable topsheets 22 are made in accordance with U.S. Pat. No. Nos. 4,609,518 and 4,629,643 which issued to Curro et al. on Sep. 2, 1986 and Dec. 16, 1986, respectively, both of which being incorporated herein by reference. Such formed films are available from The Procter & Gamble Company of Cincinnati, Ohio as "DRI-WEAVE" and from Tredegar Corporation of Terre Haute, Ind. as "CLIFF."

Preferably, the topsheet 22 is made of a hydrophobic material or is treated to be hydrophobic in order to isolate the wearer's skin from liquids contained in the absorbent core 28. If the topsheet 22 is made of a hydrophobic material, preferably at least the upper surface of the topsheet 22 is treated to be hydrophilic so that liquids will transfer through the topsheet more rapidly. This diminishes the likelihood that body exudates will flow off the topsheet 22 rather than being drawn through the topsheet 22 and being absorbed by the absorbent core 28. The topsheet 22 can be rendered hydrophilic by treating it with a surfactant or by incorporating a surfactant into the topsheet. Suitable methods for treating the topsheet 22 with a surfactant include spraying the topsheet 22 material with the surfactant and immersing the material into the surfactant. A more detailed discussion of such a treatment and hydrophilicity is contained in U.S. Pat. No. 4,988,344, issued to Reising, et al. on Jan. 29, 1991, and U.S. Pat. No. 4,988,345, issued to Reising on Jan. 29, 1991. A more detailed discussion of some suitable methods for incorporating surfactant in the topsheet can be found in US Statutory Invention Registration No. H1670, published on Jul. 1, 1997 in the names of Aziz et al. Each of these references is hereby incorporated by reference herein.

Alternatively, the topsheet 22 may include an apertured web or film which is hydrophobic. For example, the topsheet 22 may be apertured as described in U.S. Pat. No. 5,628,097, issued to Benson, et al. on May 13, 1997. Providing hydrophobicity may be accomplished by eliminating the hydrophilizing treatment step from the production process and/or applying a hydrophobic treatment to the topsheet 22, such as a polytetrafluoroethylene compound like SCOTCHGUARD or a hydrophobic lotion composition, as described below. In such embodiments, it is preferred that the apertures be large enough to allow the penetration of aqueous fluids like urine without significant resistance. Using an apertured material for the topsheet 22 also has particular advantages for absorbent articles directed to managing aqueous fecal matter.

Any portion of the topsheet 22 may be coated with a lotion as is known in the art. Examples of suitable lotions include those described in U.S. Pat. No. 5,607,760 which issued to Roe on Mar. 4, 1997; U.S. Pat. No. 5,609,587 which issued to Roe on Mar. 11, 1997; U.S. Pat. No. 5,635,191 which issued to Roe et al. on Jun. 3, 1997; and U.S. Pat. No. 5,643,588 which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 which was published on Sep. 14, 1995 in the name of Theresa Johnson. Further, the topsheet 22, the backsheet 24 or any portion of the topsheet or backsheet may be embossed and/or matte finished to provide a more cloth like appearance.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

In some cases a secondary topsheet (not shown) may be disposed between the topsheet 22 and underlying structure, such as core 28. For example, a secondary topsheet can provide a rewet barrier if it is disposed between the acquisition member 52 and the topsheet 22. Such secondary topsheets also provide beneficial horizontal distribution of deposited fluids so as to take greater advantage of the capacity of the acquisition member 52. When a secondary topsheet is used in an absorbent article in conjunction with an acquisition member 52, it is preferably sized to be at least as large as the underlying acquisition member 52. In other embodiments, a secondary topsheet may be particularly useful in combination with an apertured topsheet 22 for absorbent articles designed to be particularly effective in controlling low viscosity fecal material. Such a secondary topsheet can provide void volume for storage and dewatering of fecal material that passes through the apertures of the apertured topsheet 22. Materials suitable for use in such secondary topsheets are described in greater detail in U.S. patent application Ser. No. 09/308,430, filed on May 19, 1999, in the names of Flohr, et al. a particularly preferred embodiment described therein is a carded, resin-bonded, hydrophilic nonwoven material having a density less than about 0.055 g.cm$^3$.

3. Backsheet

The backsheet 24 is generally that portion of the diaper 20 which prevents the exudates absorbed and contained therein from soiling articles which may contact the diaper 20, such as bedsheets and undergarments. In preferred embodiments, the backsheet 24 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 24. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and U.S. Pat. No. 5,938,648 issued on Aug. 17, 1999 to LaVon et al., U.S. Pat. No. 5,865,823 issued on Feb. 2, 1999 in the name of Curro, and U.S. Pat. No. 5,571,096 issued to Dobrin et al. on Nov. 5, 1996. Each of these references is hereby incorporated by reference herein.

The backsheet 24, or any portion thereof, may be elastically extensible in one or more directions. In one embodiment, the backsheet 24 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801, which issued to Chappell, et, al. on May 21, 1996, which is incorporated herein by reference. In alternate embodiments, the backsheet 24 may comprise elastomeric films, foams, strands, or combinations of these or other suitable materials with nonwovens or synthetic films.

The topsheet 22 and the backsheet 24 are joined together about periphery 38 in any suitable manner. As used herein, the term "joined" encompasses configurations whereby the topsheet 22 is directly joined to the backsheet 24 by affixing the topsheet 22 directly to the backsheet 24, and configurations whereby the topsheet 22 is indirectly joined to the backsheet 24 by affixing the topsheet 22 to intermediate members which in turn are affixed to the backsheet 24. In a preferred embodiment, the topsheet 22 and the backsheet 24 are affixed directly to each other in the diaper periphery by attachment means (not shown) such as an adhesive or any other attachment means as known in the art. The backsheet 24 may be joined to the topsheet 22, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986, which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

4. Core

In disposable diaper 20, a preferred embodiment of the core 28 according to the present invention comprises an acquisition member 52, a distribution member 51 and a storage component 10. Each of these components serves a particular function and, therefore, each will be discussed separately below.

In order to be able to compare absorbent articles for varying end use conditions, or differently sized articles, particularly the absorbent cores thereof, the "design capacity" has been found to be a suitable measure.

For example, infants represent a typical usage group, but, even within this group, the amount of urine loading, frequency of loading, composition of the urine varies widely. For example there is not only variation between smaller infants (i.e., newborns) and toddlers, but also among various individual infants having the same general age and weight.

Other user groups include larger (older) children still suffering from incontinence and incontinent adults. Both groups can use absorbent articles, again with a wide range of loading conditions, generally referred to as light incontinence ranging up to severe incontinence.

Recognizing that one skilled in the art will readily be able to transfer the teaching herein to other sizes, the following discussion will refer to toddler sized infants. For such users, urine loading of up to 75 ml per voiding and voiding rates of 15 ml/sec have been found to be sufficiently representative. An average of four such voidings per wear period results in a total loading of 300 ml. In order to cope with such requirements an absorbent article for toddler use should have a "design capacity" with the capability of acquiring and storing such amounts of urine.

Such amounts of fluids must be absorbed by materials which can ultimately store them, or at least the aqueous parts thereof, such that little, if any, fluid is left on the surface of the article adjacent to a wearer's skin. Each such absorbent material has an "ultimate capacity" which is reached when it is equilibrated with its environment. This equilibration can be in an absorbent article under real in-use conditions after long wearing times, or in a test procedure for pure materials or material composites. As many of the processes under consideration have asymptotic kinetic behavior, one skilled in the art will readily consider "ultimate capacities" to be reached when the actual capacity has reached a value sufficiently close to the asymptotic endpoint, e.g., relative to the equipment measurement accuracy.

As is discussed above, the core 28 of the present invention comprises materials which are primarily designed to ultimately store fluids (e.g., storage component 10), and other materials which are primarily designed to fulfill other functions such as acquisition (e.g., acquisition member 52) and/or distribution (e.g., distribution member 51) of the fluid. However, it should also be recognized that each such core component also has a particular ultimate storage capability and that suitable core materials according to the present invention are described without attempting to artificially separate such functions. Nonetheless, an ultimate storage capacity can be determined for the total absorbent core 28, for regions thereof, for absorbent structures, or even sub-structures, but also for materials as being used in any such structures or components.

As noted above with respect to the various user groups, one skilled in the art will be able to readily adopt the appropriate design capacities for other intended user groups by, for example, varying the dimensions of the individual components of the absorbent article.

a. Acquisition Member

A key component of diaper 20 of the present invention is fluid acquisition member 52 which comprises a thin until wet structure according to the present invention. This fluid acquisition member 52 serves to quickly collect and temporarily hold discharged body fluid. A portion of discharged fluid may, depending upon the wearer's position, permeate the acquisition member 52 and be absorbed by the fluid absorbent member in the area proximate to the discharge. However, since fluid is frequently discharged in gushes, the fluid absorbent member in such area may not absorb the fluid as quickly as it is discharged. Therefore, the upper acquisition member 52 hereof also facilitates transport of the fluid from the point of initial fluid contact to other parts of the acquisition member 52. In the context of the present invention, it should be noted that the term "fluid" includes, but is not limited to, liquids, urine, menses, perspiration, and water based body fluids.

The fluid handling function of the acquisition member 52 is of particular importance. The acquisition member 52 must have sufficient temporary capacity to rapidly absorb a "gush" of a bodily fluid and have a CAH that is high enough to acquire body fluids from adjacent structure (e.g., to partition fluid from the topsheet 22), and sufficient fluid retention to control the acquired fluid and under the influence of gravity (i.e., CDH has a minimum satisfactory value) yet not exhibit excessive fluid retention (i.e., the CDH should not be too great) so as to make it difficult for distribution member 51 to desorb the acquisition member 52.

The acquisition member 52 may be comprised of several different materials including but not limited to: a) nonwoven or woven assemblies of synthetic fibers including polyester, polypropylene, or polyethylene, natural fibers including cotton or cellulose, blends of such fibers, or any equivalent materials or combinations of materials and b) compressed regenerated cellulosic sponges. A particularly preferred material for the fluid acquisition member 52 is the thin until wet material described above. As noted in the description of that material, it remains desirably thin until it is exposed to an aqueous liquid at which time it rapidly expands so as to absorb the liquid.

The fluid acquisition member 52 is positioned such that it is in fluid communication with topsheet 22, and serves to quickly acquire and partition body exudates from the wearer's body to an absorptive distribution member 51. Adhesive bonding of acquisition member 52 to topsheet 22 may enhance the fluid communication by providing interfacial bonding and preventing topsheet separation from impeding fluid flow.

Figure 2A:
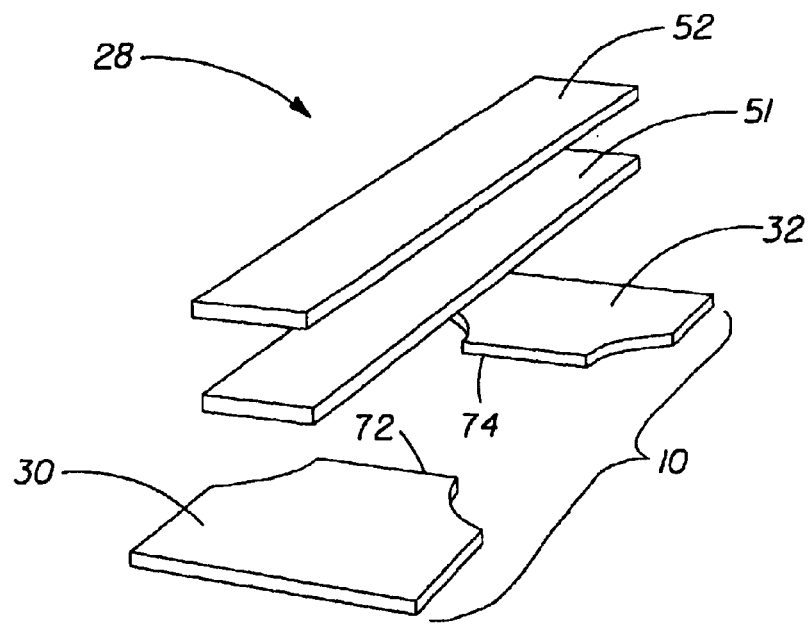
FIG. 2a of the drawings is a blown-apart view of a representative multi-layer core for inclusion in a diaper similar to that shown in FIG. 1.
Figure 2B:
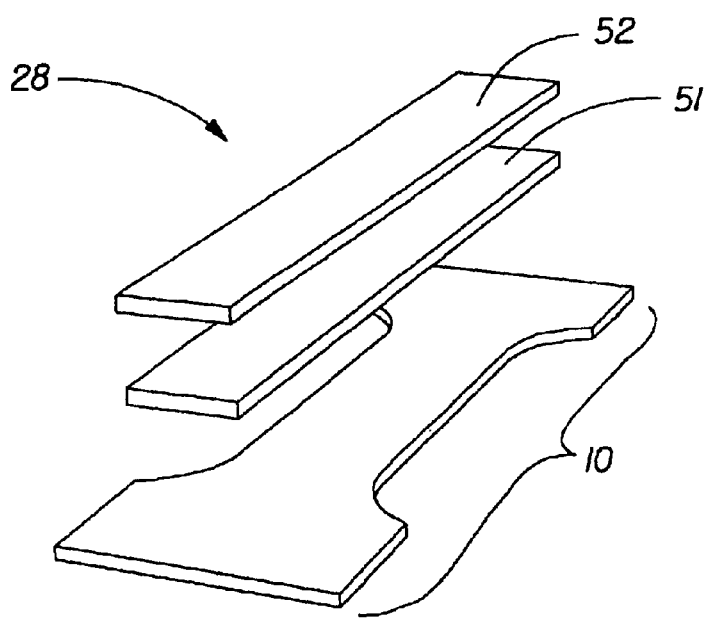
FIG. 2b of the drawings is a blown-apart view of another representative multi-layer core for inclusion in a diaper shown similar to that shown in FIG. 1.

As shown in FIGS. 1, 2a and 2b, the generally rectilinear components have a crotch width 53 corresponding to a suitable width for the crotch area 66 of a disposable diaper. As noted above, absorbent articles having a narrow crotch width 53 are particularly desirable. As used herein the "crotch width" of an absorbent article is the transverse width at the crotch point 27 of the dry absorbent article. Suitably, crotch width is less than or equal to about 9 cm. Preferably, crotch width is less than or equal to about 7 cm, more preferably less than or equal to about 5 cm. As well, the length of the respective core components may be varied to provide a suitable fit for various wearer sizes. Suitably the length is between about 10 cm and about 60 cm. While the acquisition member 52 may extend the entire longitudinal length of diaper 20 it finds its greatest utility in the crotch area 66. An exemplary length for such a crotch area positioned acquisition member 52 for a toddler sized infant is about 25 cm.

While low density fluid acquisition members can quickly collect and temporarily hold discharged body fluids, they contribute undesirable bulk to an absorbent article. Such bulk is particularly undesirable in the area between a wearer's legs. Therefore the thin until wet structures described above are particularly desirable for use as an absorbent strip 52 in diaper 20 of the present invention.

b. Distribution Member (Optional)

Distribution member 51 moves fluid in the x and y dimensions of the core 28 and is subsequently desorbed by the fluid storage component, shown generally as 10. As such, the distribution member 51 will comprise material(s) that function to distribute fluids away from the crotch area 66. (While fluid distribution is an important function of the crotch area's material, it is within the scope of the invention to include materials in the crotch area 66 whose primary function is the storage of fluids, so long as the requisite properties of the present invention are achieved.) In particular, a preferred distribution member 51 of the present articles will comprise a material that exhibits high vertical wicking capacity. The ability to wick fluid vertically, i.e., fluid wicking in a direction opposite gravitational forces, is an important performance attribute since the absorbent cores are utilized in absorbent articles in a manner such that fluid to be absorbed must be moved within the article from a relatively lower position to a relatively higher position within the absorbent core of the article. This ability to move fluid against gravity is of particular import to the present invention, given that relatively small levels of fluid are to be stored in the crotch area 66 of the core 28. Distribution members and suitable materials therefor are described in greater detail in copending, commonly assigned U.S. patent application Ser. No. 08/825,072, filed Mar. 27, 1997 by G. Young et al., Ser. No. 08/825,071, filed Mar. 27, 1997 by G. LaVon et al., and Ser. No. 08/826,208, filed Mar. 27, 1997 by G. Young et al., the disclosure of each being incorporated herein by reference.

While acquisition member 52 and distribution member 51 are shown in FIGS. 1, 2a and 2b generally as being rectilinear and of equal size, other shapes and size relationships may be utilized. In a rectilinear configuration the distribution member can suitably be between about 50 and about 70 mm wide (i.e., crotch width 53 is between about 50 and about 70 mm) and extend the full longitudinal length of the diaper 20 (typically about 40 cm for a diaper 20 designed for a toddler sized infant).

With regard to fluid handling, the distribution member 51 will comprise a material having a vertical wicking capacity of at least about 15 g/g, preferably at least about 25 g/g, still more preferably at least about 40 g/g, at a height of 2 cm. Alternatively, the distribution member 51 will comprise a material having a vertical wicking absorbent capacity at a height of 20 cm of at least about 10 g/g, preferably at least about 20 g/g, more preferably at least about 30 g/g, still more preferably at least about 40 g/g. Alternatively, the material will have a vertical wicking absorbent capacity at a height of 25 cm of at least about 5 g/g, preferably at least about 15 g/g, more preferably at least about 20 g/g, still more preferably at least about 30 g/g. Alternatively, the material will have a vertical wicking absorbent capacity at a height of 30 cm of at least about 0.5 g/g, preferably at least about 10 g/g, more preferably at least about 20 g/g, still more preferably at least about 30 g/g. It should be understood that while the above definitions are provided in the alternative, a single material may possess more than one of these attributes.

Preferred materials for distribution member 51 can be readily desorbed by other components of the absorbent core that store such fluids, including those comprising conventional absorbent gelling materials such as are disclosed in, for example, U.S. Pat. No. 5,061,259 (Goldman et al.), issued Oct. 29, 1991, U.S. Pat. No. 4,654,039 (Brandt et al.), issued Mar. 31, 1987 (reissued Apr. 19, 1988 as Re. 32,649), U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference; as well as absorbent macrostructures made from these absorbent gelling materials such as those disclosed in, for example, U.S. Pat. No. 5,102,597 (Roe et al.), issued Apr. 7, 1992, and U.S. Pat. No. 5,324,561 (Rezai et al.), issued Jun. 23, 1994, both of which are incorporated by reference). Indeed, these distribution materials can be most readily desorbed by absorbent polymeric foams that store the acquired fluid, such as those disclosed in, for example, U.S. Pat. No. 5,268,224 (DesMarais et al.), issued Dec. 7, 1993; U.S. Pat. No. 5,387,207 supra, U.S. Pat. No. 5,563,179 supra; U.S. Pat. No. 5,560,222 (DesMarais et al.), issued Jul. 22, 1997, and copending U.S. patent application Ser. No. 09/042,429, filed Mar. 13, 1998 by T. A. DesMarais; and mixtures of absorbent gelling materials with the aforementioned polymeric foams or other absorbents of very high surface areas such as those described in co-pending U.S. patent application Ser. Nos. 09/041,930 and 09/042,435, both filed Mar. 13, 1998 by G. A. Young et al.; the disclosure of each of which is incorporated by reference.

One suitable material for providing the requisite wicking properties for the distribution member 51 is an open-celled absorbent polymeric foam material that is derived by polymerizing a High Internal Phase Water-in-Oil Emulsion (hereafter referred to a HIPE). Such polymeric foams may be formed to provide the requisite storage properties, as well as the requisite distribution properties. Where distinct storage materials are included in the front and rear sections of the core 28, the polymeric distribution foams will preferably exhibit desorption properties that allow these other core components (having higher absorption pressures than the desorption, pressure of the distribution foam) to partition away fluid. It is desirable that this component keep the wearer's skin dry, even in "gush" situations and even when subjected to a compressive load; is soft, flexible and comfortable to the wearer of the absorbent article; and has a relatively high capacity for fluid so as to provide diapers and other absorbent articles that efficiently utilize core components.

HIPE-derived foams which provide the requisite distribution properties for use herein are described in copending U.S. patent application Ser. No. 08/563,866 (DesMarais et al.), filed Nov. 25, 1995 (hereafter referred to as "'866 application"); U.S. Pat. No. 5,387,207 (Dyer et al.), issued Feb. 7, 1995; and U.S. Pat. No. 5,260,345 (DesMarais et al.), issued Nov. 9, 1993; the disclosure of each of which is hereby incorporated by reference.

Polymeric foams useful in the present invention are those which are relatively open-celled. This means the individual cells of the foam are in communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2 in the '866 application. As used herein, a foam material is "open-celled" if at least 80% of the cells in the foam structure that are at least 1 $\mu$m in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures.

The polymeric foams can be prepared in the form of collapsed (i.e., unexpanded), polymeric foams that, upon contact with aqueous fluids, expand and absorb such fluids. See, for example, copending U.S. patent application Ser. No. 08/563,866 and U.S. Pat. No. 5,387,207. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. Non-collapsible foams, such as those described copending U.S. patent application Ser. No. 08/542,497 and U.S. Pat. No. 5,260,345 are also useful as the distribution material.

It has been found that the specific surface area per foam volume of the polymeric foam is particularly useful for empirically defining foam structures that will remain in a collapsed state. Furthermore, this property is important to the material's ability to provide the vertical wicking absorbent capacities discussed herein. See U.S. Pat. No. 5,387,207, where specific area per foam volume is discussed in detail. "Specific surface area per foam volume" refers to the capillary suction specific surface area of the foam structure times its foam density in the expanded state. Polymeric foams useful for use as a distribution member 51 in the present invention will preferably have a capillary suction specific surface area of at least about 0.01 $m^2/cc$, more preferably at least about 0.03 $m^2/cc$. Typically, the capillary suction specific surface area is in the range from about 0.01 to about 0.20 $m^2/cc$, preferably from about 0.03 to about 0.10$m^2/cc$, most preferably from about 0.04 to about 0.08 $m^2/cc$. Example 5 demonstrates the use of such HIPE-based distribution members.

Another suitable material for use specifically as the distribution material 51 in the crotch area 66 of the present article is described the aforementioned U.S. Pat. No. 5,800,416. These fiber-based distribution materials, referred to therein as "fluid absorbent members", preferably comprise three basic components: chemically stiffened, twisted, and curled bulking fibers, high surface area fibers, and chemical binder additive, each of which is described in detail. The fibrous members described utilize a high surface area fiber to provide capillary pressure (or suction) to the fluid absorbent member. These high surface area fibers are generally low diameter and can be highly conformable. They provide the fibrous member with capillary pressure well in excess of the capillary pressure found in the bulk-providing chemically stiffened, twisted, and curled fibers (unrefined) alone. Preferred fibers for this high surface area application are the eucalyptus family of wood pulp fibers. Particularly suitable eucalyptus fibers include those of the eucalyptus grandis species.

The fibrous members preferably comprise from about 80% to about 95% of the chemically stiffened, twisted, and curled fibers, from about 3% to about 20% of a high surface area fiber, and from 0% to about 5% of a chemical additive binding means for increasing physical integrity of the structure. (All percentages refer to weight percentages based on total dry weight.) Preferably, the fluid absorbent members will comprise between about 80% and about 90% of chemically stiffened, twisted, and curled fibers, between about 8% and about 18% of a hugh surface area fiber (hereafter described), and between about 0.25% and about 2% of a chemical additive binding means. More preferably, the fluid absorbent members comprise about 88% chemically stiffened, twisted, and curled fibers, about 10% high surface area fibers, and about 2% chemical binding means. A particularly preferred distribution member 51 of this type is a wetlaid chemically bonded web as explained above having a basis weight of 150 $g/m^2$ and a density of 0.094 $g/cm^3$, consisting of a fiber blend of: 90% by weight of chemically-stiffened, twisted cellulose, commercially available under the designation "CMC" from Weyerhaeuser Co. of Federal Way, Wash. and 10% by weight of eucalyptus fibers that is bonded by 2% by weight of the fiber blend using a polyacrylamide-glyoxal resin marketed by Cytec Industries, West Patterson, N.J. under the trade name Parez™ 631 NC. The properties of an absorbent core structure having such a distribution member are described in Example 3.

In addition to the use of a chemical binding means, fluid absorbent members may also benefit from the integration of a thermally bonded polymer into the material. This structure is formed by polymer bonding fibers (such as Hoechst-Celanese Copolyolefin Bicomponent fiber and the like) strongly bonding at fiber intersections. In these embodiments, the thermoplastic binding material provides bond sites at intersections of the binding fibers with either other binding fibers, chemically stiffened, twisted, and curled cellulosic fibers, or high surface area fibers. Such thermally bonded structures can, in general, be made by forming a fibrous assembly comprising the stiffened cellulosic fibers and thermoplastic fibers, which are preferably evenly distributed throughout. The thermoplastic fibrous material can be intermixed with the stiffened cellulosic fibers and fine fibers in the aqueous slurry prior to web formation. Once formed, the web is thermally bonded by heating the assembly until the thermoplastic portion of the fibers melt. Specific non-limiting examples of suitable fibrous materials include polyester hot melt fibers (KODEL 410), bicomponent fibers (CELBOND®), tricomponent fibers, mixtures thereof, and the like. An exemplary structure of this type is a wet-laid, heatbonded structure having a basis weight of 150 gsm and a density of 0.105 g/cm3, consisting of 45% by weight of chemically-stiffened, twisted cellulose (CS), commercially available under the designation "CMC" from Weyerhaeuser Co.; 45% by weight of eucalyptus fibers; and 10% by weight of CELBOND® from Hoechst Celanese Corporation, US, type 255, having a dTex of about 3.3, a denier of about 3.0. and a fiber length of about 6.4 mm. The properties of an absorbent core structure having such a distribution member are described in Example 4.

c. Storage Component

Any material capable of desorbing the distribution member 51 may be utilized as the storage component 10. For example, the storage component 10 may comprise hydrogel-forming polymers that are water-insoluble, but water-swellable and are capable of absorbing large quantities of fluids. Such polymers are commonly referred to as "hydrocolloids" or "superabsorbent" materials, and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful herein have a multiplicity of anionic, functional groups, such as sulfonic acid, and more typically carboxy groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Olefinically unsaturated carboxylic acid and carboxylic acid anhydride monomers include the acrylic acids typified by acrylic acid itself, methacrylic acid, ethacrylic acids α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Storage materials comprising hydrogel-forming polymers can also comprise fibrous materials to form fibrous assemblies or fibrous matrices. Fibers useful herein include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers.

The fibers used can be hydrophilic, hydrophobic or can be a combination of both hydrophilic and hydrophobic fibers. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled *Contact Angle, Wettability and Adhesion,* edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

For storage materials useful herein, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

An alternative material suitable for use as a storage component 10 of the present invention comprises a polymeric foam material derived from HIPEs. These materials will preferably have is sufficient absorption pressures to desorb the material used for the distribution member 51, thereby providing reduced fluid storage in the crotch region of the article. However, as indicated, a single material may function as both the distribution and storage material in the present articles.

The foams described above with respect to the distribution member 51 of the present invention are also useful as a material for the storage component 10. Particularly preferred are collapsible polymeric foam materials that, upon contact with aqueous fluids (in particular aqueous body fluids such as urine), can expand and absorb these fluids. These absorbent polymeric storage foam materials comprise a hydrophilic, flexible, nonionic polymeric foam structure of interconnected open-cells as disclosed in, for example, U.S. Pat. No. 5,387,207 (Dyer et al.), issued Feb. 7, 1995, and copending U.S. patent application No. 08/563,866 (DesMarais et al.), filed Nov. 25, 1995, the disclosure of each of which is hereby incorporated by reference.

The storage foam material useful in the present invention provides very low density absorbent foams. For a given expanded thickness, these lower density foams more efficiently utilize the available polymer material. As a result, the lower density absorbent foams provide an economically attractive means for achieving thinner absorbent cores for absorbent articles such as diapers, adult incontinence pads or briefs, sanitary napkins, and the like. This is achieved while providing desired absorbency and mechanical properties.

As will be recognized, the storage component 10 can comprise blends or combinations of any of the materials identified above as being suitable for use therein. Preferred blends of a HIPE-derived form material and a hydrogel polymer are described in copending, commonly assigned U.S. patent application Ser. No. 09/258,889, filed in the names of Young, et al. on Mar. 1, 1999, the disclosure of which is incorporated herein by reference. Described therein are storage components 10 having between 15 and 98% HIPE-derived foam and 25 and 99% hydrogel polymer, such as is available as ASAP 2300 (available from Chemdal LTD), Arlington Heights, Ill.). A preferred storage component comprises between 20% and 50% HIPE-derived foam and 50% and 80% hydrogel polymer. A particularly preferred combination structure for the storage component 10 comprises a combination of a HIPE-derived foam material as described above and an absorbent hydrogel polymer, such as the aforementioned ASAP 2300. In this particularly preferred structure, storage elements 30, 32 comprise a structure wherein the HIPE-derived foam material underlies the distribution member 51 and the absorbent hydrogel polymer overlies the distribution member 51. Preferably, the absorbent hydrogel polymer is joined to the distribution member 51 using an effective amount of a melt blown adhesive material. Optionally, a layer of a low basis weight tissue (not shown) may be disposed between the acquisition member 52 and the distribution member and overlying the hydrogel portion of the storage component 10 in order to better retain the hydrogel on the distribution member 51.

As is shown in FIGS. 1 and 2*a,* storage component 10 can comprise two separate storage components 30 and 32 that are disposed such that there is no absorbent storage member component located in crotch area 66 of the diaper 20. Because such an absorbent core 28 has little or no fluid storage material (it should be recognized that the distribution member 51 may have significant storage capacity and will contain fluid, at least until it is desorbed by a higher suction storage material) in the center of the core (corresponding to the crotch or fluid discharge region of the core), articles containing such cores may provide improved fit and wearer comfort both when the article is dry and after it has received several loadings of body fluid. See, e.g., co-pending U.S. patent application Ser. No. 08/825,072, filed Mar. 27, 1997 by G. Young et al., co-pending U.S. patent application Ser. No. 08/825,071, filed Mar. 27, 1997 by G. LaVon et al., and co-pending U.S. patent application Ser. No. 08/826,208, filed Mar. 27, 1997 by G. Young et al.

FIG. 2*a* depicts a blown-apart view of absorbent core 28 having two separated elements 30 and 32, each of which consists of a storage absorbent member that will desorb distribution material 51. Front panel 32 generally corresponds to the portion of the disposable, diaper worn in the front of the wearer. Similarly, the back panel 30 corresponds to the portion of the disposable diaper worn in the back of the wearer. In an alternative design where the absorbent core comprises separate fluid storage elements (similar to elements 30 and 32 in FIG. 1 and FIG. 2*a*), the distribution layer may be positioned below both the acquisition layer(s) and the storage components. That is, referring to FIG. 1, distribution material 51 would be located below acquisition material 52 and storage elements 30 and 32.

Alternatively, storage component 10 may be a unitary layer(s) (i.e., where the dashed lines 70 in FIG. 1 indicate that storage component 10 is included in the fluid discharge region of the article) of storage material. Such an embodiment of an absorbent core 28 is depicted in FIG. 2*b*.

d. Combining Core Members to Form Core Structures

Core structures suitable for use as a core 28 using the members as described above can be arrangements of one or more of these of one or more of each of these component types. Such structures can be in flat form, or can comprise the individual components in other three-dimensional forms. The individual components can be in direct contact, or can be spaced apart—provided, that they remain in liquid communication (As used herein, a component is in liquid communication if a body fluid that is disposed on one of the components of an absorbent article can transfer from that component to another component of the absorbent article—either directly or indirectly through an intervening component. Such transfer can be by capillary flow, gravimetric flow, osmotic pressure or other means as may be known.).

As will be recognized, the most simple core 28 according to the present invention can essentially consist only of a thin until wet material according to the present invention, provided it has an adequate ultimate capacity and fluid distribution properties for the intended use. Alternatively, the core 28 can comprise an acquisition member 51 which comprises a thin until wet material according to the present invention and at least one other core component which provides the distribution and storage properties described above. In particular, it is desirable that the absorbent core 28 have distribution and storage properties such that the crotch area 66 has a crotch capacity that is less than about 40% of the total capacity of the absorbent core 28 when measured using the Total Absorbent Capacity and Crotch Percent Capacity method described in the Test Methods Section below. Preferably the crotch capacity is less than about 30% or the total capacity, more preferably less than about 25%. Said another way, the crotch 28 of the present invention has storage and distribution properties such that the crotch area 66 has a lower fluid storage capacity than the remainder of the absorbent core (i.e., the difference between the total capacity and the crotch capacity is greater than the crotch capacity).

As noted in the discussion above and shown in FIGS. 1 and 2*a* and 2*b,* a particularly preferred structure for the core 28 comprises an acquisition member 52*a* distribution member 51 and a storage component 10 (FIG. 1). Such a preferred design option provides the basic structure described above with both distribution functionality (distribution member 51) and a storage structure (i.e., storage component 10). Preferably, as shown in FIGS. 1, 2*a,* and 2*b,* distribution member 51 is positioned between the two layers. Each of the topsheet and the various core components are also in liquid communication with each other.

A preferred embodiment entails a further separation of the various absorbent core components. This preferred absorbent core comprises an acquisition layer comprising the thin until wet materials of the present invention only around the crotch area 66 to manage the initial rapid fluid gush. Distribution member 51 is positioned vertically to the front and back of the acquisition member 52 so as to wick the fluid out of the crotch area 66, not just from the front to the back. A distinct storage component 10 is positioned in a position above the acquisition layer (with an assumed standing position of the wearer) and is in contact only with the distribution member 51 (FIG. 2*a*). The storage absorbent component 10 then must be able to absorb the fluid from the distribution member 51, overcoming both the force due to gravity and that due to the desorption pressures of the distribution material. The product so depicted (FIGS. 1 and 2*a*) removes fluid from the crotch area 66 within the time provided between insults, leaving the acquisition member 52 relatively dry and ready for further uptake of fluid. This further maintains the shape of the garment and keeps the crotch area relatively dry for better skin health.

Alternative embodiments of absorbent cores according to the present invention can comprise layered structures wherein, in cross section, an acquisition layer comprising a thin until wet structure according to the present invention overlies a storage layer with or without a distribution layer therebetween. Such structures have many of the benefits described in relation to the preferred structure discussed above and are contemplated as being part of the present invention.

5. Other Components

Tape tab fasteners 65 are typically applied adjacent edge 63 in the rear of diaper 20 to provide a fastening means for holding the diaper on the wearer. The tape tab fasteners 65 depicted are representative only. The tape tab fasteners can be any of those well known in the art, such as the fastening tape disclosed in U.S. Pat. No. 3,848,594 (Buell), issued Nov. 19, 1974, which is incorporated by reference. These tape tab fasteners or other diaper fastening means are typically applied near the corners of the diaper 20.

Elastic members 69 are disposed adjacent the periphery of the diaper 20, preferably along each longitudinal edge 64, so that the elastic members tend to draw and hold the diaper 20 against the legs of the wearer. Additionally, elastic members 67 can be disposed adjacent either or both of the waistband regions (i.e., the region adjacent edges 63) of the diaper 20 to provide a waistband as well as or rather than leg cuffs. For example, a suitable waistband is disclosed in U.S. Pat. No. 4,515,595 (Kievit et al.), issued May 7, 1985, which is incorporated by reference. In addition, a method and apparatus suitable for manufacturing a disposable diaper having elastically contractible elastic members is described in U.S. Pat. No. 4,081,3011 (Buell), issued Mar. 28, 1978, which is incorporated by reference.

The elastic members are secured to the diaper 20 in an elastically contractible condition so that in a normally unrestrained configuration, the elastic members effectively contract or gather the diaper 20. The elastic members can be secured in an elastically contractible condition in at least two ways. For example, the elastic members can be stretched and secured while the diaper 20 is in an uncontracted condition. Alternatively, the diaper 20 can be contracted, for example, by pleating, and the elastic members secured and connected to the diaper 20 while the elastic members are in their unrelaxed or unstretched condition. The elastic members may extend along a portion of the length of the diaper 20. Alternatively, the elastic members can extend the entire length of the diaper 20, or any other length suitable to provide an elastically contractible line. The length of the elastic members is dictated by the diaper design.

Other components (not shown) as are well known to the art, such as barrier cuffs, elasticized side panels, and the like, are also compatible with the diaper 20 of the present invention and may be used as desired.

In use, the diaper 20 is applied to a wearer by positioning the rear portion of diaper 20 under the wearer's back, and drawing the remainder of the diaper 20 between the wearer's legs so that the front portion is positioned across the front of the wearer. The tape-tab 65 or other fasteners are then secured preferably to outwardly facing areas of the diaper 20. In use, disposable diapers or other absorbent articles incorporating the fluid absorbent members of the present invention tend to more quickly and efficiently distribute and store fluid and to remain dry due to the high absorbent capacity of the fluid absorbent members. Disposable diapers incorporating the fluid absorbent members of the present invention can also be thinner and more flexible.

As referred to herein, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, tampons, bandages, facial tissues, paper towels, and the like.

IV. Test Methods

The following is a detailed description of the various methods used to characterize the present invention. It will be recognized that with respect to test methods B, C, and D, where the test material lacks sufficient integrity to withstand the testing protocol, a hydrophobic screen that does not impact wicking performance can be used to support the material.

A. Synthetic Urine

The test fluid to be used for the testing described in the other methods is synthetic urine (syn-urine). This aqueous composition comprises the following components dissolved in distilled water:

| Component | Percentage |
|---|---|
| KCl | 2.0 g/L |
| $Na_2SO_4$ | 2.0 g/L |
| $(NH_4)H_2PO_4$ | .85 g/L |
| $(NH_4)_2HPO_4$ | .15 g/L |
| $CaCl_2$ | .19 g/L |
| $MgCl_7$ | .23 g/L |

B. Density

1. Compressed Dry Density (CDD)

One procedure which can be used to determine foam density is that described in ASTM Method No. D3574-86, Test A, which is designed primarily for the testing of urethane foams but which can also be utilized for measuring the density of the structures of the present invention. In particular, density measurements made according to this ASTM procedure are carried out on samples which have been preconditioned in as specified in the ASTM test. Density is determined by measuring both the dry mass of a given sample (DSM) and its volume at 22°±2° C. Dimensions of the fibrous samples can be measured using a dial-type or digital gauge as are commercially available (e.g. an Ames model 482 dial-type caliper gauge as is available from Ames Co.; Waltham, Mass. or a Ono-Sokki model EG-225 digital caliper gauge as is available from Ono-Sokki Co., Ltd.; Japan) using a pressure on the dial foot of 1.4 kPa (0.2 psi). Density is calculated as mass per unit volume. For purposes of this invention, density is generally expressed in terms of $g/cm^3$.

2. Expanded Wet Density (EWD)

In this measurement, the sample is saturated with synthetic urine at zero hydrostatic head (A saturated sample from the Capillary Sorption test described below may be used, if desired). The volume is measured in this fully expanded state and the dry mass of the sample (DSM) is measured. The density upon saturation with synthetic urine is thus calculated as dry mass per wet volume, expressed in terms of $g/cm^3$.

C. Capillary Sorption

1. Purpose and Overview

The purpose of this test is to measure the capillary sorption absorbent capacity, as a function of height, of absorbent members of the present invention. Capillary sorption is a fundamental property of any absorbent that governs how liquid is absorbed and desorbed by the absorbent structure.

In the Capillary Sorption experiment, capillary sorption absorbent capacity is measured as a function of fluid pressure due to the height of the sample relative to the test fluid reservoir (hydrostatic head). A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic heads) is measured. Incremental absorption occurs due to the incremental lowering of the frit (i.e., increasing capillary suction). Similarly, incremental desorption occurs as the frit is raised. This test is intended to determine the height at which an absorbent structure acquires 50% of its absorbent capacity (CAH) from an unloaded starting head of 100 cm and the height at which the structure retains 50% percent of the absorbent capacity (CDH) thereof after the structure has been saturated at a zero head ($Wt_{ZH}$). As will be recognized the same test methodology can be used to determine the amount of fluid absorbed or desorbed by an absorbent material on a grams fluid/gram material basis at any selected height within the heights described below. Such data is reported as capillary sorption absorption capacity at the selected height (for example, a capillary sorption absorption capacity of 15 g/g at 35 cm would be reported as CSAC 35=15 g/g). Acquisition begins with an unloaded sample at a starting head of 100 cm. The head is incrementally decreased in order to fully saturate the sample at zero head ($Wt_{ZH}$) and, after the structure is saturated at zero head, the head is incrementally increased to desorb the saturated structure. Absorbent capacity at each increment is measured and a plot of capacity vs. desorption height is used to determine CAH and CDH.

2. Method

The method described in U.S. patent application Ser. No 09/258,889, filed in the name of Young, et al. on Mar. 1, 1999 is used with the following exceptions:

a. Absorption starts at a 100 cm head and then incrementally decreased to saturate the sample at zero head followed by desorption back to 100 cm instead of measuring incremental absorption beginning at a 200 cm head. The sample height is then again incrementally decreased to zero head for a second absorption curve.

b. A medium porosity glass frit having 10–15 micron pores is used rather than a frit having 4–5.5 micron pores.

c. The medium porosity glass frits are not jacketed and the temperature of the synthetic urine is not equilibrated to 31° C. but rather maintained at 22.2° C. (72° F.) by use of a constant temperature room d. Setup Height Value: 100 cm e. Finish Height Value: 0 cm f. Hydrostatic Head Parameters: 100, 80, 60, 50, 45, 40, 35, 30, 25, 20, 16, 14, 12, 10, 8, 6, 4, 2, 0, 2, 4, 6, 8, 10, 12, 14, 16, 20, 25, 30, 35, 40, 45, 50, 60, 80, 100, 80, 60, 50, 45, 40, 35, 30, 25, 20, 16, 14, 12, 10, 8, 6, 4, 2, 0.

g. Equilibrium Samples=10.0 h. Equilibrium Constant=0.001

D. Compressed Initial Z-Direction Expansion Rate

Overview

The z-direction expansion rate and expansion factor can be quantified for purposes of this invention by monitoring the change in the caliper of a sample as it is saturated with synthetic urine and expanded to a resulting wet caliper. The sample is held under a confining pressure of 0.2 psi (1.4 kPa)

Test Apparatus and Fluids

Electric Caliper Gage

Ono-Sokki model EG-225 available from Ono-Sokki Co., Ltd.; Japan with 1 square inch (6.45 cm$^2$) foot.

Interface

Computer interface for data collection. The interface must be able to collect data at a rate of at lease one data point every 0.4 seconds.

Weights

Sufficient weight of a size to fit on the foot to provide a confining pressure of 0.2 psi (1.4 kPa)

Synthetic Urine

Prepared according to Test Method A above. The synthetic urine used to saturate the sample is heated to 92° F. (33.3° C.).

Sample Support

A 2 inch (5.1 cm) diameter X 0.25 inch (0.0.64 cm) thick, channeled (0.06 inch (0.16 cm) wide X 0.06 (0.16 cm) inch deep with a 0.125 inch (0.32 cm) repeat) porous (0.04 inch (0.10 cm) holes with a 0.188 inch (0.48 cm) repeat in a direction parallel to the channels and a 0.125 inch (0.32 cm) repeat in a direction perpendicular to the channels) support (suitable construction materials include stainless steel and aluminum), a test stand which holds the support such that the synthetic urine is free to flow through the holes in the support, and a reservoir to hold the synthetic urine as it is provided to the sample as described in the method below.

Sample Preparation

Sample Dimensions

Samples are die cut or formed to have a 3.55 in$^2$ (22.9 cm$^2$) circular surface area Equilibration Samples are equilibrated for at least two hours at 22±2° C., 50% RH prior to testing.

Method

1. Center the sample on the porous support and center the foot of the caliper gauge on the sample.

2. Measure the initial dry caliper ($Clp_{initial}$) under the 0.2 psi confining pressure.

3. Begin to pour synthetic urine into the reservoir at a rapid but controlled rate, being careful not to splash liquid onto the sample. Synthetic urine addition is continued until the test sample is fully immersed in the test fluid.

4. Begin data from the caliper gauge when the fluid level in the reservoir is half way up the stainless steel sample support but not yet contacting the compressed sample. Caliper readings during the first two minutes of the test are acquired at a frequency of 1 data point every 0.4 seconds during time=0–20 seconds, 1 data point every 5 seconds during time=20–30 seconds, and 1 data point every 10 seconds during time=30–120 seconds.

5. After the initial 2 minutes, the caliper foot is removed from the sample and it is allowed to acquire fluid under no confining pressure for 1 minute.

6. The gauge foot is placed back on the sample with a confining pressure of 0.09 psi and the caliper measured after the sample is allowed to equilibrate for 30 seconds.

7. The 0.2 psi confining pressure is returned and the caliper is measured again after the sample equilibrates for another 30 seconds.

Calculations and Data Reporting

Z-Direction Expansion Factor can be determined from the initial dry caliper ($Clp_{initial}$) and the expanded wet caliper after 120 seconds ($Clp_{final}$) according to the following calculation:

Z-Direction Expansion Factor=$Clp_{final}/Clp_{initial}$

Z-Direction Expansion Rate can be determined from the time ($T_{90\%}$) it takes to expand to 90% of the expanded wet caliper after 120 seconds ($Clp_{final}$), the expanded wet caliper at 90% ($Clp_{90\%}$) of the expanded wet caliper after 120 seconds ($Clp_{final}$), the expanded wet caliper at 90% ($Clp_{90\%}$) of the expanded wet caliper after 120 seconds ($Clp_{final}$) according to the following calculation:

Compressed Initial Z-Direction Expansion Rate=$(Clp_{90\%}-Clp_{initial})/(T_{90\%})$ Report Time to 90% Expansion ($T_{90\%}$) and Compressed Initial Z-Direction Expansion Rate E. Capacity Capacity can be determined by dividing the equilibrium mass of synthetic urine absorbed at a zero hydrostatic head ($Wt_{ZH}$) by the dry mass of the sample (DSM) and is expressed as grams fluid per gram of dry sample.

F. Capacity per Dry Unit volume

The capacity per dry unit volume (CPDUV) can be determined from the equilibrium mass of synthetic urine absorbed at zero head ($Wt_{ZH}$), the compressed dry density (CDD), and the dry sample mass (DSM) according to the following calculation:

$$CPDUV = \frac{Wt_{ZH} \times CDD}{DSM}$$

G. Crotch Point

FIG. 3 illustrates the means for determining the crotch point of an article and its absorbent core. Referring to FIG. 3, the legs of a standing wearer are depicted crossectionally as 301 and 302. A continuous material 303 (e.g., a string or rubber band) is twisted once and is placed around the wearer's legs at a point sufficiently close to the wearer's torso such that the intersection 304 of material 303 can be extrapolated onto the article being worn. The crotch point of the core of the article is thereby determined, and the crotch region of the core is determined per the above description.

H. Bulk Softness

Overview

Figure 4:
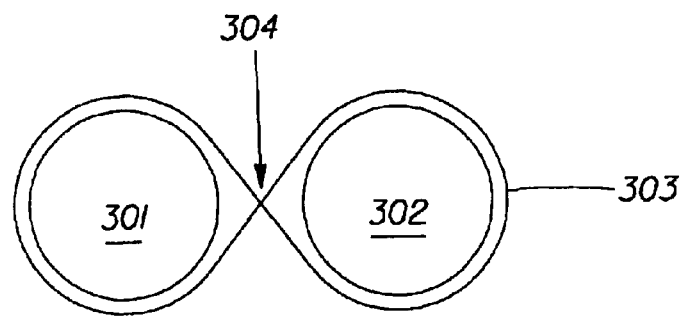
FIG. 4 illustrates how the crotch point of a wearer, an absorbent article and the corresponding absorbent core are determined

This method is intended to measure individual materials as well as structures comprising these materials. The method uses a tensile tester in compressive mode and a sample holder (FIGS. 4a and 4b) to measure the buckling force for a sample.

Apparatus

Tensile Tester:

A suitable tensile tester is available from Zwick Company of Ulm, Germany as a Zwick Material Tester type 144560.

Figure 3A:
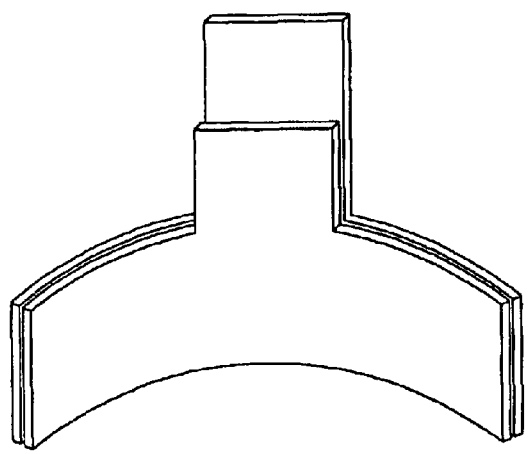
FIG. 3a is a perspective view of the clamp pair used in the Bulk Softness test method.
Figure 3B:
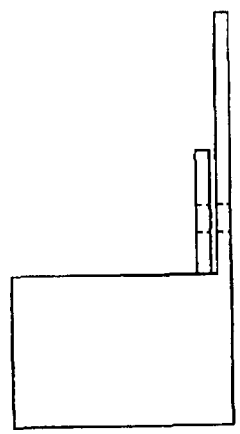
FIG. 3b is a side view of the clamp pair used in the Bulk Softness test method.

Sample Holder:

The sample holder for this test is shown in FIGS. 3a and 3b. As can be seen therein the sample is held between two curvilinear (The curvature of the outer element of the holder has a radius of 59 mm±1 mm with an arc length of 150 mm and the inner element has a radius of 54 mm±1 mm with an arc length of 140 mm) plates that have tabs 30 mm wide that extend upward 20 mm (front element) and 55 mm (rear element) so as to enable insertion of the sample holder into the jaws of the tensile tester. The equipment is designed to test various material thickness from 1 mm up to 10 mm. As will be recognized, sample holders of this type are necessary for both the upper and lower jaws of the tensile tester. As will be apparent to those skilled in the art, modifications to the clamp design described above may be necessary for samples having a caliper larger than 10 mm. When making such modifications, it is important to confine the sample between elements that maintain the same sample radius of curvature while not creating wrinkles in the sample.

Sample Preparation

Prior to testing a sample is conditioned under controlled conditions (50% RH, 25° C.) for at least two hours.

The sample is cut to 60 mm ×150 mm (±2 mm per dimension). The sample dimensions, short side vs. long side, should be consistent with the material orientation when used in a finished product (i.e., if the material in use has a short dimension and a long dimension then the sample should be cut such that the short side of the sample is the same relative side as in the overall material).

Apparatus Setup

1. Calibrate the tensile tester (in compressive mode) according to the manufacturer's instructions.
2. Set the compression rate to 200 mm/minute. Set the crosshead stop point to 30 mm.
3. Insert a sample into the sample holder to a depth of 7 mm±1 mm for each clamp set.
4. Set the tensile tester jaw separation so that the unconstrained portion of the sample is smooth and unbuckled. This corresponds to a spacing between the upper and lower portions of the sample holder of 46 mm.

Operation and Data Collection

1. Insert the sample/sample holder assembly into the jaws of the tensile tester.
2. Operate the tensile tester in compressive mode to record a force/compression curve for each sample.
3. Record the buckling force for each sample. Buckling force is defined as follows:
   a) If the force as a function of compression reaches an initial maximum or peak value and then levels or even decreases again for higher compressions, this peak force is defined as the buckling force. This curve shape can be typically seen on bonded materials and marks the point at which the structure is collapsing. Further compression will later again typically increase the force as the material is compressed throughout its entire structure
   b) If the force as a function of compression is strongly monotonic (i.e. does not show a local maximum in the mathematical sense), then the buckling force of the material is defined as the force at which the force vs. compression curve changes its curvature. This curve shape can be typically seen for unbonded materials or structures.

The definitions for a) and b) can also be expressed in a mathematical sense as follows: Let f(x) be the mathematical function describing force (f) measured gas a function of compression (x), then the compression value $x_b$ (i.e., the compression at which the buckling occurs) and at which buckling force is defined can be determined as follows: for case a) $x_b$ is the compression at which the first derivative of the function f is zero, i.e., $df/dx$ $(x=x_b)=0$; for case b) $df/dx$ does not approach zero but shows a local maximum; this means that $x_b$ is the compression at which the second derivative becomes zero, i.e., $d^2f/dx^2$ $(x=x_b)=0$ 4. Repeat steps 1–3 for at least 5 samples for each structure tested and report the average and standard deviation of the buckling force.

I. Total Capacity and Crotch Percent Capacity

The following protocol is intended to provide the Total Absorbent Capacity ("TAC") as well as, the Crotch Region Capacity ("CRC") of the article. The protocol uses data obtained from in-use testing of articles by panelists.

Panelist Selection

Panelists should be recruited by weight, within the intended size range of the articles being tested. Currently, the product sizes and baby weights for marketed Pampers, Luvs and Huggies are as follows (as of Mar. 25, 1997):

| Diaper Size | New-born | Small | Small/ Medium | Medium | Large | X-Large |
|---|---|---|---|---|---|---|
| Pampers | up to 10 lbs | 8–14 lbs | 12–18 lbs | 16–28 lbs | over 22 lbs | over 27 lbs |
| Luvs | na | 8–15 lbs | 12–18 lbs | 16–28 lbs | 21–37 lbs | over 30 lbs |
| Huggies | up to 10 lbs | 8–14 lbs | 12–18 lbs | 16–28 lbs | 22–37 lbs | over 30 lbs |

A group of 100 panelists should be recruited uniformly across the appropriate weight range relative to the size of article being tested and the intended user group. Note: the above sizes are for currently marketed articles and may change as article designs and or sizes are modified.

Following the recruiting step, 30 panelists are to be selected from the group at random.

Article Set-up

The test articles are weighed to provide a dry article weight.

The panelist removes the article the child is wearing when the test begins, i.e., the panelist's own article, and the panelist applies the test article, in the panelist's normal fashion.

Once the test article is applied, the panelist places the wearer in the standing position and the crotch point is determined as previously described in this application.

The crotch point is then marked on the outside of the test article in a permanent fashion.

The loading zone is then determined by measuring from the crotch point forward to the appropriate genital point relative to the sex and size of the wearer. The distance forward from the crotch point for females in the medium size is 1.25 inches. The distance forward from the crotch point for males in the medium size range is 2.5 inches.

It is apparent to one skilled in the art that these distances may increase or decrease with the size of the wearer. Therefor, for the other sizes, the distance can be determined by placing the wearer in a standing position and determining the crotch point as specified previously, and then measuring from the crotch point to the urethra or base of the penis.

Once the loading zone is determined, the distance from the front waist to the loading zone is measured; this distance is used to establish the length of the loading tube to,be inserted into the article during the syn-urine loading.

Synthetic Urine

The test fluid to be used for the test is synthetic urine (syn-urine) as described in Test Method A above:

The temperature in the syn-urine bath is to be held at 37° C. A suitable heated bath is Lauda M20-B available from VWR Scientific Products.

Delivery pumps are to be used to pump the syn-urine from the heated bath to the article. The volume and rate of delivery is to be 75 ml at 15 ml/sec. Suitable pumps include Masterflex Models 7550-60 or 7524-00 available from Cole Palmer Instrument Company. The inner diameter of the loading tube is to be 0.125 inch.

Protocol

Once the articles are applied and marked as described above, loose fitting blue cotton pants are weighed to provide a dry pants weight and then the pants are applied over the test article so that leakage can be easily identified and measured.

The test articles are then loaded by inserting the loading tube to the predetermined distance, as measured from the waist, and applying the specified loading at the specified rate.

Between loads, the wearer returns to normal activity.

The articles are loaded with the specified load and rate at a frequency between loads consistent with infant urination frequencies.

These loadings are continued until about 1 gram of fluid leaks from the article onto the cotton pants. This can be determined by removing the pants and weighing them.

Once at least 1 gram of fluid has leaked onto the pants, the test article is removed and is immediately weighed.

Total Capacity and Crotch Percent Capacity

The total capacity for a given test article is determined by subtracting the dry article weight of the given article from the wet article weight of that same article.

The total capacity for the group is the average of the total capacities of the individual articles.

Crotch region capacity is determined by laying the loaded article flat and cutting the crotch region out of the article. (The crotch region is determined relative to the crotch point which was previously identified for the article.) This region is then weighed. This procedure should be conducted within 15 minutes of removal of the article from the wearer.

A corresponding crotch region is cut from a dry article to provide a dry crotch region weight.

The crotch capacity is determined by subtracting the dry crotch region weight from the wet crotch region weight. This provides the crotch capacity for a given article.

The crotch capacity for the group of articles is considered to be the average of the individual crotch region capacities.

The crotch region capacity as a percent of the total is determined by dividing the average crotch region capacity by the average total capacity for a given set of articles.

A similar procedure is used to determine the percent absorbent capacity of the absorbent core behind the crotch point.

VI. Representative Examples

These examples illustrate the specific structures according the present invention.

EXAMPLE 1

This example demonstrates making fibrous thin until wet materials according to the present invention.

Individualized crosslinked cellulose fibers, as described in U.S. patent application Ser. No. 08/692,352, filed in the name of Herron, et al. on Aug. 5, 1996, are formed into a wetlaid handsheet by slurrying a mixture of the crosslinked fibers, Crill, and Parez® 631NC wet strength resin in a headbox, depositing the mixture onto a forming wire, and dewatering the structure by passing it over a vacuum slit. The fibrous web is then placed in an oven and heated at 120° C. for 60 minutes to completely dry the structure and cure the wet strength resin. The dried fibrous assembly comprises 90% crosslinked fibers, 8% Crill, and 2% Parez® (zero water basis). The wetlaid structures formed in the above manner had basis weights of 500–600 grams/m². Samples of the wetlaid materials having a circular surface area of 3.55 in² (22.9 cm²) are die cut for further treatment.

A temporary binder (polyacrylic acid sodium salt (PAA-Na) or polyvinyl alcohol (PVA)) is applied to certain wetlaid samples by spraying a 10 weight percent aqueous solution of the resin onto the sample (A hand held aerosol spray unit, such as is available from Precision Valve Corp. of Yonkers, N.Y. is convenient). As will be recognized a solution add-on equal to the fiber weight will provide about 10% dry solids. In some instances, vacuum is applied to the sample during application of the binder to improve binder penetration into the wetlaid web and to partially evaporate the water of application (Conditions g to n).

After application of the binder, the wetlaid samples are placed in a shimmed platen press, such as is available from Fred S. Carver, Inc. of Menomonee Falls, Wis. as a Model C Press that is equipped with heating plates as are available from VWR Scientific of Chicago, Ill. as catalog no. 538814-007. Treated and untreated control samples are densified by compression to a fixed separation between the plates (defined by the shims) to a predetermined in-process density. The samples remain under compression until no more weight loss is observed upon further heating of the sample (Typically, the samples remain under compression at 120° C. for 3–7 minutes). Compressed samples are removed from the heated press, and allowed to cool to room temperature.

Table 1 compares various wet laid structures prepared as described above.

TABLE 1

| Condition | Structure Description | In-Process Density (g/cc) | Compressed Density* (g/cc) | Compression Stability (Ratio of Compressed to In-Process Density) |
|---|---|---|---|---|
| a | Airlaid Crosslinked Fibers with no temporary binder[1] | 0.185 | 0.089 | 0.48 |
| b | Wetlaid Structure with no temporary binder[1] | 0.205 | 0.112 | 0.55 |
| c | Wetlaid Structure with no temporary binder[1] | 0.297 | 0.149 | 0.50 |
| d | Wetlaid Structure treated with water in a manner similar to the binder treatment | 0.206 | 0.174 | 0.84 |
| e | Wetlaid Structure treated with 11% PAA-Na[2] add-on | 0.199 | 0.191 | 0.96 |
| f | Wetlaid Structure treated with 11% PAA-Na[2] add-on | 0.296 | 0.277 | 0.94 |
| g | Wetlaid Structure treated with 11% PVA add-on with vacuum[3] | 0.200 | 0.188 | 0.94 |
| h | Wetlaid Structure treated with 5% PVA add-on using vacuum[3] | 0.211 | 0.180 | 0.85 |
| I | Wetlaid Structure treated with water in a manner similar to the binder treatment using vacuum | 0.210 | 0.159 | 0.76 |

[1]Control
[2]Polyacrylic acid, sodium salt as is available from Poly Sciences, Inc. of Warrington, PA as catalog no. 6568 (nominal $M_w$ = 2,100)
[3]Polyvinyl alcohol as is available from Aldrich Chemical, Co. of Milwaukee, WI as catalog no. 36,06-7 (nominal $M_w$ = 9,000–10,000)

EXAMPLE 2

This example demonstrates the expansion and fluid handling properties of fibrous thin until wet materials according to the present invention.

Additional structures are made according to the method of Example 1 and evaluated according to the various methods described in the Test Methods section. Table 2 displays the results of evaluating the rate and degree of expansion from the densified state of thin until wet materials treated with either 5% PAA-Na or PVA temporary binder. Table 3 displays the results of evaluating similarly treated materials according to the Capillary Sorption Test described previously in the test methods section.

TABLE 2

| Condition | Sample | Compressed Dry Density (g/cc) | Expanded Wet Density (g/cc) | Ratio | Time to 90% Expansion (sec) | Compressed Initial Z-Direction Expansion Rate (mm/sec) |
|---|---|---|---|---|---|---|
| m | Wetlaid Structure treated with 5% PAA-Na[1] using vacuum | 0.172 | 0.078 | 2.2 | 5.5 | 0.55 |
| n | Wetlaid Structure treated with 5% PVA[2] using vacuum | 0.167 | 0.079 | 2.1 | 6.1 | 0.57 |

TABLE 3

| Condition | Sample | Capacity (g/g) | CPDUV (g/dry cc) | CDH (cm) |
|---|---|---|---|---|
| m | Wetlaid Structure treated with 5% PAA-Na[1] using vacuum | 10.5 | 1.8 | 20 |

TABLE 3-continued

| Condition | Sample | Capacity (g/g) | CPDUV (g/dry cc) | CDH (cm) |
|---|---|---|---|---|
| n | Wetlaid Structure treated with 5% PVA[2] using vacuum | 10.4 | 1.6 | 12 |

[1]Polyacrylic acid, sodium salt as is available from Polysciences, Inc. of Warrington, PA as catalog no. 6568 (nominal $M_w$ = 2,100)
[2]Polyvinyl alcohol as is available from Aldrich Chemical, Co. of Milwaukee, WI as catalog no. 36,062-7 (nominal $M_w$ = 9,000–10,000)

EXAMPLE 3

This example demonstrates the use of a fibrous thin until wet material according to the present invention in a first absorbent structure. The following absorbent core structure is prepared:

Acquisition member using a material according to Condition m of Example 2. The acquisition member is 5 cm×25 cm.

A distribution member which underlies the acquisition member and comprises a wetlaid chemically bonded web as explained above having a basis weight of 150 g/m² and a density of 0.094 g/cm³, consisting of a fiber blend of: 90% by weight of chemically-stiffened, twisted cellulose, commercially available under the designation "CMC" from Weyerhaeuser Co. of Federal Way, Wash. and 10% by weight of eucalyptus fibers that is bonded by 2% by weight of the fiber blend using a polyacrylamide-glyoxal resin marketed by Cytec Industries, West Patterson, N.J. under the trade name Parez™ 631 NC. The distribution member has a caliper of about 1.2 mm and is 5 cm×40 cm.

A two element storage component which lies adjacent to the distribution member and comprises a blend of HIPE-derived foam and an absorbent hydrogel polymer (ASAP 2300 available from Chemdal LTD, Arlington Heights, Ill.). The storage component is about 50% by weight HIPE-derived foam and about 50% by weight hydrogel polymer. Such a structure is described in greater detail as Example 5 in the aforementioned U.S. patent application Ser. No. 09/258,889. Each of the elements of the storage component is about 75 mm×130 mm and underlies the distribution member in a configuration similar to the one shown in FIG. 1 with the storage elements being positioned in the front and rear of the diaper leaving the crotch area substantially absent of storage material On exposure to an aqueous fluid, the acquisition member rapidly absorbs the insult with substantially no runoff, the distribution member carries the fluid from the crotch area of the core toward the ends where it is stored in the storage component.

EXAMPLE 4

This example demonstrates the use of a fibrous thin until wet material according to the present invention in a second absorbent structure. The following absorbent core structure is prepared:

Acquisition member using a material according to Condition n of Example 2. The acquisition member is 5 cm×25 cm.

A distribution member which underlies the acquisition member and comprises a wet-laid, heatbonded structure having a basis weight of 150 gsm and a density of 0.105 g/cm3, consisting of 45% by weight of chemically-stiffened, twisted cellulose (CS), commercially available under the designation "CMC" from Weyerhaeuser Co. 45% by weight of eucalyptus fibers; and 10% by weight of CELBOND® from Hoechst Celanese Corporation, US, type 255, having a dTex of about 3.3, a denier of about 3.0, and a fiber length of about 6.4 mm. The distribution member has a caliper of about 1.2 mm and is 5 cm×40 cm.

A multi element storage component which both underlies and overlays the distribution member. The underlying portion of the storage component comprises a HIPE-derived foam material and is situated in a configuration similar to the configuration of the storage component of Example 3. The overlaying portion of the storage component comprises an absorbent hydrogel polymer (ASAP 2300 available from Chemdal LTD, Arlington Heights, Ill.) that is joined to the upper (body facing) surface of the distribution member using a melt blown adhesive material. A low basis weight tissue ply is also disposed between the acquisition member and the distribution member such that it overlays the absorbent hydrogel polymer.

On exposure to an aqueous fluid, the acquisition member rapidly absorbs the insult with substantially no runoff, the distribution member carries the fluid from the crotch area of the core toward the ends where it is stored in the storage component.

EXAMPLE 5

This example demonstrates the use of a fibrous thin until wet material according to the present invention in a third absorbent structure. The following absorbent core structure is prepared:

Acquisition member using a material according to Condition m of Example 2. The acquisition member is 5 cm×25 cm.

A HIPE-derived open cell foam distribution member which underlies the acquisition member made according to U.S. patent application Ser. No. 09/042,418, filed in the name of DesMarais, et al. on Mar. 13, 1998. The foam has a specific surface area per foam volume greater than 0.1 m²/cc. The distribution member has a caliper of about 1.2 mm and is 7 cm×40 cm.

A multi element storage component which both underlies and overlays the distribution member. The underlying portion of the storage component comprises a HIPE-derived foam material and is situated in a configuration similar to the configuration of the storage component of Example 3. The overlaying portion of the storage component comprises an absorbent hydrogel polymer (ASAP 2300 available from Chemdal LTD, Arlington Heights, Ill.) that is joined to the upper (body facing) surface of the distribution member using a melt blown adhesive material. A low basis weight tissue ply is also disposed between the acquisition member and the distribution member such that it overlays the absorbent hydrogel polymer.

On exposure to an aqueous fluid, the acquisition member rapidly absorbs the insult with substantially no runoff, the distribution member carries the fluid from the crotch area of the core toward the ends where it is stored in the storage component.

EXAMPLE 6

This example demonstrates preparation and properties of compressed, regenerated cellulosic sponge-based thin until wet acquisition materials according to the present invention. In this example commercially available sponge materials from Spontex (material no. 12330 (1.6 cm expanded thickness) and material no.12334 (2.5 cm expanded thickness)) and an experimental sponge (no material number available) were evaluated using the various test methods listed herein. Conditions a used material no. 12330. Material no. 12334 was fully expanded, washed as described below and cut to a thickness of about 1 cm using a band saw while still moist to prepare conditions d and e which have a lower basis weight (see sample preparation procedure below). As noted above, both materials comprise the same material composition (pore size distribution, etc.), the only differences being material thickness and lot to lot variation typical of a commercial material. Reduced basis weight conditions j and k were also provided by cutting the experimental sample when moist.

Sample Preparation

The following sample preparation steps were conducted for all samples prior to evaluation:

1) Fully expand the commercially available sponge by saturating it with deionized water.
2) Wash the expanded sponge with deionized water to remove residual soluble materials
3) If desired, cut the moist sponge to a thickness that yields a predefined basis weight using a band saw.
4) Dry the washed sponge.
5) If desired, compress the dried sponge to a predefined density using a shimmed platen press, such as is available from Fred S. Carver, Inc. of Menomonee Falls, Wis., that is heated to a temperature 120° C.

The prepared samples were then evaluated for various physical and fluid handling properties using the methods listed herein. The results of this evaluation are listed in Tables 4, 5, and 6.

TABLE 4

Compressed Regenerated Cellulose Sponge Physical Properties

| Cd'n | Sample ID | Basis Weight (grams/m$^2$) | Compressed Dry Density (grams/cm$^3$) | Expanded Wet Density (grams/cm$^3$) | Ratio |
|---|---|---|---|---|---|
| a | Spontex Mtl. 12330 As Received | 889 | 0.647 | 0.091 | 6.2 |
| b | Spontex Mtl. 12330 Fully Expanded | 879 | 0.061 | 0.052 | 1.0 |
| c | Spontex Mtl. 12330 Dry Compressed | 864 | 0.284 | 0.062 | 4.0 |
| d | Spontex Mtl. 12334 Dry Compressed | 470 | 0.288 | 0.066 | 3.8 |
| e | Spontex Mtl. 12334 Dry Compressed | 466 | 0.351 | 0.066 | 4.7 |
| f | Spontex Experimental As Received | 791 | 0.808[b] | 0.087 | 9.3 |
| g | Spontex Experimental Fully Expanded | 770 | 0.060[c] | 0.058 | 1.0 |
| h | Spontex Experimental Dry Compressed | 727 | 0.276 | 0.066 | 4.2 |
| i | Spontex Experimental Dry Compressed | 704 | 0.365 | 0.068 | 5.3 |
| j | Spontex Experimental Dry Compressed | 560 | 0.289 | 0.061 | 4.2 |
| k | Spontex Experimental Dry Compressed | 582 | 0.354 | 0.061 | 5.1 |

TABLE 5

Compressed Regenerated Cellulose Sponge Fluid Handling Properties

| Cd'n | Sample ID | Capacity (grams/gram) | CDH (cm) | CPDUV (grams/dry cm$^3$) |
|---|---|---|---|---|
| a | Spontex Mtl. 12330 As Received | 7.4 | 16.7 | 4.8 |
| b | Spontex Mtl. 12330 Fully Expanded | 11.9 | 9.0 | 0.7 |
| c | Spontex Mtl. 12330 Dry Compressed | 10.8 | 11.2 | 3.1 |
| d | Spontex Mtl. 12334 Dry Compressed | 9.4 | 9.6 | 2.7 |
| e | Spontex Mtl. 12334 Dry Compressed | 9.4 | 9.3 | 3.3 |
| f | Spontex Experimental As Received | 8.8 | 15.8 | 7.1 |
| g | Spontex Experimental Fully Expanded | 13.6 | 11.1 | 0.8 |
| h | Spontex Experimental Dry Compressed | 11.1 | 13.7 | 3.1 |
| i | Spontex Experimental Dry Compressed | 10.8 | 13.8 | 3.9 |
| j | Spontex Experimental Dry Compressed | 10.5 | 11.2 | 3.0 |
| k | Spontex Experimental Dry Compressed | 10.8 | 11.4 | 3.8 |

TABLE 6

Compressed Regenerated Cellulose Sponge Expansion Properties

| Cd'n | Sample ID | Time to 90% Expansion (sec) | Compressed Initial Z-Direction Expansion Rate (mm/sec) |
|---|---|---|---|
| a | Spontex Mtl. 12330 As Received | 4.4 | 2.22 |
| c | Spontex Mtl. 12330 Dry Compressed | 2.8 | 2.99 |
| d | Spontex Mtl. 12334 Dry Compressed | 2.4 | 2.26 |
| e | Spontex Mtl. 12334 Dry Compressed | 2.3 | 2.34 |
| f | Spontex Experimental As Received | 4.0 | 2.77 |
| i | Spontex Experimental Dry Compressed | 2.2 | 4.26 |

EXAMPLE 7

This example demonstrates the use of a sponge-based thin until wet material according to the present invention in a first absorbent structure. The following absorbent core structure is prepared:

Acquisition member using a material according to Condition e of Example 6.The acquisition member is 5 cm×25 cm.

A distribution member which underlies the acquisition member and comprises a wetlaid chemically bonded web as explained above having a basis weight of 150 g/m² and a density of 0.094 g/cm³, consisting of a fiber blend of: 90% by weight of chemically-stiffened, twisted cellulose, commercially available under the designation "CMC" from Weyerhaeuser Co. of Federal Way, Wash. and 10% by weight of eucalyptus fibers that is bonded by 2% by weight of the fiber blend using a polyacrylamide-glyoxal resin marketed by Cytec Industries, West Patterson, N.J. under the trade name Parez® 631 NC. The distribution member has a caliper of about 1.2 mm and is 5 cm×40 cm.

A two element storage component with the elements being separated by the distribution member. The first element comprises a HIPE-derived foam). The HIPE-derived foam underlies the distribution member and has a basis weight of about 160 grams/m². The second element comprises an absorbent hydrogel polymer (ASAP 2300 available from Chemdal LTD, Arlington Heights, Ill. overlies the distribution member and has basis weight of about 300 grams/m². Each of the elements of the storage component is positioned in both the front and rear of the diaper leaving the crotch area substantially absent of storage material. Such a structure is described in greater detail as Example 1 of PCT application Serial No. WO 99/55264 published in the name of Procter & Gamble on Nov. 4, 1999.

On exposure to an aqueous fluid, the acquisition member rapidly absorbs the insult with substantially no runoff, the distribution member carries the fluid from the crotch area of the core toward the ends where it is stored in the storage component.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the invention. It is therefore intended to cover in the appended claims all such changes and modification that are within the scope of this invention.

What is claimed is:

1. A thin until wet material suitable for use as an acquisition layer in an absorbent article, the material comprising a blend of fibers, said fibers consisting of a blend of crosslinked cellulosic fibers and high surface area cellulosic fibers, said material further comprising polymeric temporary binding means and a wet strength means, said material being held in a compressed state by said temporary binding means until exposure to an aqueous liquid, wherein:

when said material is saturated by an aqueous fluid, said material has an expanded wet density of between about 0.04 grams/cm³ and about 0.4 gram/cm³ and a medium capillary desorption height (CDH) of less than about 25 cm;

said temporary binding means helps maintain said material at a compressed dry density of between about 0.06 grams/cm³ and about 1.2 grams/cm³ until said material is exposed to an aqueous fluid wherein, upon such exposure, said temporary binding means releases so that said material expands at a compressed initial z-direction expansion rate of at least about 0.5 millimeters/second; and the ratio of said compressed dry density to said expanded wet density is greater than about 1.5:1.

2. A thin until wet material according to claim 1 wherein said expanded wet density is between about 0.04 grams/cm³ and about 0.1 grams/cm³.

3. A thin until wet material according to claim 1 wherein said material has a CDH of less than about 20 cm.

4. A thin until wet material according to claim 3 wherein said material has a CDH of less than about 12 cm.

5. A thin until wet material according to claim 1 wherein said compressed dry density is between about 0.06 grams/cm³ and about 0.4 grams/cm³.

6. A thin until wet material according to claim 1 wherein said ratio of said compressed dry density to expanded wet density said is greater than about 2:1.

7. A thin until wet material according to claim 6 wherein said ratio of said compressed dry density to said expanded wet density is greater than about 2.5:1.

8. A thin until wet material according to claim 1 wet strength means is selected from the group consisting of wet strength resins, bicomponent fibers, powdered adhesives, and combinations thereof.

9. A thin until wet material according to claim 8 wherein said wet strength means comprises a wet strength resin.

10. A thin until wet material according to claim 1 wherein said wet strength resin comprises a polyamide epichlorohydrin resin.

11. A thin until wet material according to claim 1 wherein said temporary binding means comprises a water soluble or water dispersible polymer.

12. A thin until wet material according to claim 11 wherein said water soluble or water dispersible polymer is selected from the group consisting of polyacrylic acid and copolymers and salts thereof; polymethacrylic acid and copolymers and salts thereof; polyvinyl alcohol; starch; modified cellulose; modified starch; modified cellulose; gum acacia/gum arabic; soluble gelatin; and mixtures thereof.

13. A thin until wet material according to claim 12 wherein said water soluble or water dispersible polymer is selected from the group consisting of polyacrylic acid and copolymers and salts thereof; polymethacrylic acid and copolymers and salts thereof; polyvinyl alcohol; and mixtures thereof.

14. A thin until wet material according to claim 1 wherein said high surface area fibers have a Canadian Standard Freeness of less than about 200.

15. A thin until wet material according to claim 14 wherein said high surface area fibers comprise crill.

16. An absorbent core for an absorbent article said absorbent core comprising:

an acquisition member, said acquisition member comprising a thin until wet material wherein said thin until wet material comprising a blend of fibers, said fibers consisting of a blend of crosslinked cellulosic fibers and high surface area cellulosic fibers, said material further comprising wet strength means, and polymeric temporary binding means wherein:

said wet strength means connects at least a portion of the individual fibers forming said assembly such that, when said material is saturated by an aqueous fluid, said material has an expanded wet density of between about 0.04 grams/cm$^3$ and about 0.5 grams/cm$^3$ and a CDH of less than about 25 cm;

said temporary binding means helps maintain said material at a compressed dry density of between about 0.06 grams/cm$^3$ and about 1.2 grams/cm$^3$ until said material is exposed to an aqueous fluid wherein, upon such exposure, said temporary binder releases so that said material expands at a compressed initial z-direction expansion rate of at least about 0.5 millimeters/second; and the ratio of said compressed dry density to said expanded wet density is greater than about 1.5:1; and at least one additional core component in fluid communication with said acquisition member.

* * * * *

UNITED STATES PATENT AND TRADEMARK OFFICE
CERTIFICATE OF CORRECTION

PATENT NO. : 6,746,976 B1
DATED : June 8, 2004
INVENTOR(S) : Edward Joseph Urankar et al.

It is certified that error appears in the above-identified patent and that said Letters Patent is hereby corrected as shown below:

Column 1,
Line 28, delete "sane" and insert -- same --.

Column 6,
Line 23, delete "(CDM)" and insert -- (CDH) --.
Line 24, delete "Chatterjee" and insert -- Chatterjee, --.
Line 56, delete "material" and insert -- materials --.

Column 8,
Line 22, delete "material" and insert -- material, --.

Column 10,
Line 30, delete "Heron," and insert -- Herron, --.

Column 12,
Line 67, delete "material's" and insert -- materials --.

Column 18,
Line 40, delete "airlaid" and insert -- air-laid --.

Column 20,
Line 21, delete "No. Nos." and insert -- Nos. --.

Column 21,
Line 49, delete "0.055 g.cm$^3$" and insert -- 0.055 g/cm$^3$ --.

Column 26,
Line 32, delete "desorption," and insert -- desorption --.

Column 27,
Line 67, delete "hugh" and insert -- high --.

Column 28,
Line 41, delete "0.105 g/cm3," and insert -- 0.105 g/cm$^3$, --.
Line 47, delete "3.0" and insert -- 3.0, --.

Column 31,
Line 10, delete "LTD)," and insert -- LTD, --.
Line 50, delete "disposable," and insert -- disposable --.

UNITED STATES PATENT AND TRADEMARK OFFICE
CERTIFICATE OF CORRECTION

PATENT NO. : 6,746,976 B1
DATED : June 8, 2004
INVENTOR(S) : Edward Joseph Urankar et al.

It is certified that error appears in the above-identified patent and that said Letters Patent is hereby corrected as shown below:

Column 33,
Line 30, delete "4,081,3011" and insert -- 4,081,301 --.
Line 61, delete "fluid" and insert -- fluids --.

Column 34,
Line 32, delete "$MgCl^7$" and insert -- $MgCl^2$ --.

Column 38,
Line 59, delete "gas" and insert -- as --.

Column 39,
Line 66, delete "to,be" and insert -- to be --.

Column 41,
Lines 39-40, delete "538814-007." and insert -- 53881-007. --.

Column 42,
Line 25, delete "36,06-7" and insert -- 36,062-7 --.

Column 44,
Line 1, delete "0.105 g/cm3," and insert -- 0.105 g/cm$^3$, --.

UNITED STATES PATENT AND TRADEMARK OFFICE
CERTIFICATE OF CORRECTION

PATENT NO.   : 6,746,976 B1
DATED        : June 8, 2004
INVENTOR(S)  : Edward Joseph Urankar et al.

It is certified that error appears in the above-identified patent and that said Letters Patent is hereby corrected as shown below:

Column 45,
Line 11, delete "Conditions a" and insert -- Conditions a-c --.

Column 47,
Line 12, delete "Parez®" and insert -- Parez$^{TM}$ --.
Line 50, delete "modification" and insert -- modifications --.

Signed and Sealed this

Twenty-eighth Day of February, 2006

JON W. DUDAS
*Director of the United States Patent and Trademark Office*